(12) United States Patent
Berthier et al.

(10) Patent No.: US 8,835,002 B2
(45) Date of Patent: Sep. 16, 2014

(54) STABLE FORMALDEHYDE-FREE MICROCAPSULES

(75) Inventors: Damien Berthier, Geneva (CH); Géraldine Leon, Geneva (CH); Nicolas Paret, Geneva (CH)

(73) Assignee: Firmenich SA, Geneva (CH)

( * ) Notice: Subject to any disclaimer, the term of this patent is extended or adjusted under 35 U.S.C. 154(b) by 30 days.

(21) Appl. No.: 13/702,377

(22) PCT Filed: Jun. 21, 2011

(86) PCT No.: PCT/IB2011/052700
§ 371 (c)(1),
(2), (4) Date: Dec. 6, 2012

(87) PCT Pub. No.: WO2011/161618
PCT Pub. Date: Dec. 29, 2011

(65) Prior Publication Data
US 2013/0084456 A1 Apr. 4, 2013

Related U.S. Application Data

(60) Provisional application No. 61/358,741, filed on Jun. 25, 2010.

(30) Foreign Application Priority Data

Jun. 25, 2010 (EP) .................................... 10167348

(51) Int. Cl.
*A61L 9/012* (2006.01)
*C08G 12/32* (2006.01)

(52) U.S. Cl.
USPC ...... 428/402.24; 528/245; 528/129; 528/156; 510/516; 510/438; 510/130

(58) Field of Classification Search
USPC .......... 512/4, 5; 510/441, 473, 475, 476, 521, 510/101, 516, 438, 130; 528/245; 428/402–402.24, 403, 404, 407; 427/31, 389.9, 212, 213.3–213.36, 427/483, 256; 264/534, 5, 41, 4–4.7; 424/408, 450, 451, 455, 93.7, 184.1, 424/497, 489, 501, 490, 491, 492, 493, 494, 424/495

See application file for complete search history.

(56) References Cited

U.S. PATENT DOCUMENTS

| | | | | |
|---|---|---|---|---|
| 5,691,426 A | * | 11/1997 | Floyd ............................ | 525/491 |
| 6,201,095 B1 | | 3/2001 | Floyd et al. ................... | 528/254 |
| 2007/0123442 A1 | | 5/2007 | Holzner et al. ............... | 510/101 |
| 2008/0227675 A1 | | 9/2008 | Struillou et al. .............. | 510/101 |
| 2010/0247941 A1 | | 9/2010 | Wilhelm et al. ........... | 428/537.5 |
| 2010/0323938 A1 | * | 12/2010 | Ouellet et al. ................ | 510/101 |

FOREIGN PATENT DOCUMENTS

| | | |
|---|---|---|
| EP | 1 065 227 A2 | 1/2001 |
| EP | 1 637 188 A1 | 3/2006 |
| JP | 2005-068202 A | 3/2005 |
| WO | WO 2006/131846 A1 | 12/2006 |
| WO | WO 2007/135108 A1 | 11/2007 |
| WO | WO 2009/100553 A1 | 8/2009 |

OTHER PUBLICATIONS

International Search Report and Written Opinion of the International Searching Authority, application No. PCT/IB2011/052700 mailed Sep. 7, 2011.

* cited by examiner

*Primary Examiner* — James J Seidleck
*Assistant Examiner* — S. Camilla Pourbohloul
(74) *Attorney, Agent, or Firm* — Winston & Strawn LLP

(57) ABSTRACT

Water-dispersible core-shell microcapsules that are essentially free of formaldehyde. Also, oligomeric compositions of, and microcapsules obtained from, particular reaction products between a polyamine component and a particular mixture of glyoxal and a $C_{4-6}$ 2,2-dialkoxy-ethanal. These compositions and microcapsules can be used as part of a perfuming composition or of a perfumed consumer product.

19 Claims, 10 Drawing Sheets

STABLE FORMALDEHYDE-FREE MICROCAPSULES

TECHNICAL FIELD

Figure 1A:
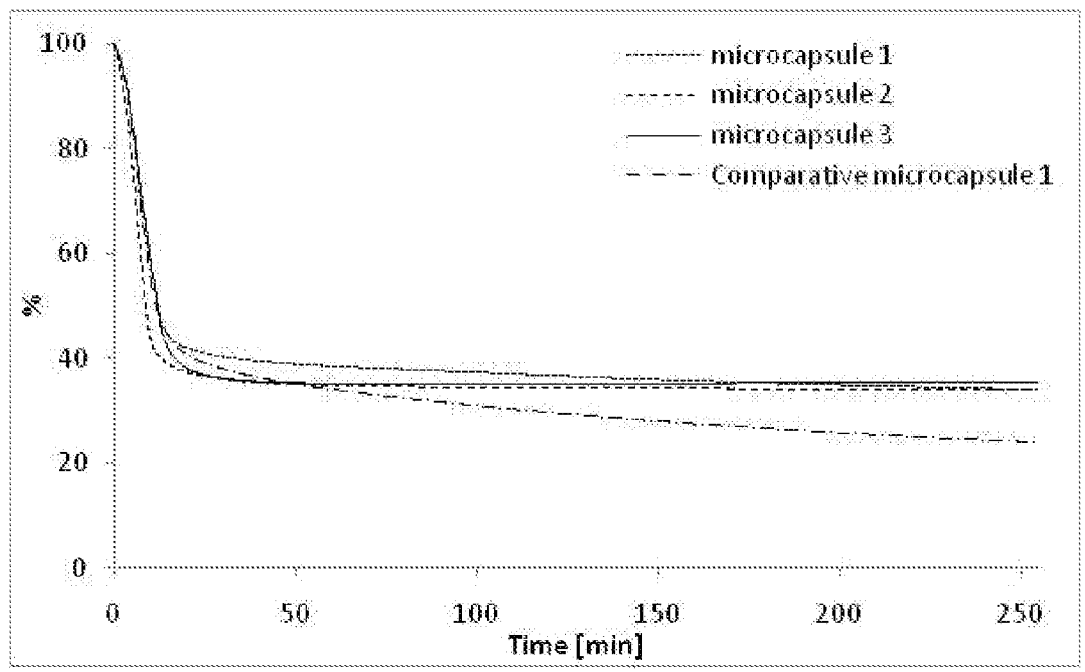

The present invention relates to the field of perfumery. More particularly, it concerns water-dispersible core-shell microcapsules essentially free of formaldehyde.

The present invention comprises also the invention's core-shell microcapsules as part of a perfuming composition or of a perfuming consumer product.

PRIOR ART

Microcapsules are a widely known type of products, generally used as carrier of a liquid phase.

A specific type of said microcapsules is the so-called aminoplast microcapsules comprising an external wall obtained by reacting a polyamine (in general melamine, i.e. 2,4,6-triamino-1,3,5-triazine) and an aldehyde (almost always in fact formaldehyde). These microcapsules are very useful in the case where the liquid core is a volatile compound or composition, like perfumes, since they are able to break under certain conditions liberating the volatile in a controlled manner.

However said capsules, which are essentially formaldehyde based, contain always residual amounts of free formaldehyde due to unreacted precursors or a slow decomposition of the thermoset oligomers. Oligomers which are formaldehyde-free are nowadays desired due to regulatory concerns, therefore there is a need by the industry for formaldehyde free core-shell microcapsules possessing performance similar to the formaldehyde based ones, which have the best performance in stability and product delivery.

Some attempts to obtain formaldehyde free microcapsules have been published in the prior art. The most relevant one for the present invention is disclosed in WO 2009/100553. The systems described in this document comprise an aminoplast oligomer obtained by reacting at least a polyamine and unclearly defined "substituted methylene moieties" which are exemplified by hemi-acetal of glyoxal esters or by 2,2-dimethoxy-ethanal (DME) or 2,2-diphenoxy-ethanal. In the facts, all capsules concretively described are obtained by reacting melamine (as unique polyamine) and DME or methyl 2-hydroxy-2-methoxy-acetate as "substituted methylene moieties". However we found that the performances and stability of such capsules are not satisfactory for an industrial application, as shown further below in the Examples.

In relation to the oligomer of the present invention, it is worth mentioning WO 07/135108. In this document there are disclosed resins obtained by reacting an amine (e.g. melamine, urea, and mixture thereof) with a glyoxal monoacetal only (e.g. DME). Said resins are different chemicals compared to the oligomers of the present invention, by their chemical structure and molecular weight, and are used in the manufacture of ligneous materials, and the application for microcapsules is not evocated or suggested.

Therefore there is still a need for core-shell microcapsules formaldehyde-free and having superior stability performances.

DESCRIPTION OF THE INVENTION

We have now surprisingly discovered a new type of formaldehyde-free oligomers which are particular suitable for the preparation on core-shell microcapsules, containing an oil core and having superior stability compared to the prior art formaldehyde-free core-shell microcapsules of similar constitution.

Therefore a first object of the present invention is an oligomeric composition comprising the reaction product of, or obtainable by reacting together:
1) a polyamine component in the form of melamine or of a mixture of melamine and at least one $C_{1-4}$ compound comprising two $NH_2$ functional groups;
2) an aldehyde component in the form of a mixture of glyoxal, a $C_{4-6}$ 2,2-dialkoxy-ethanal and optionally a glyoxalate, said mixture having a molar ratio glyoxal/$C_{4-6}$ 2,2-dialkoxy-ethanal comprised between about 1/1 and 10/1; and
3) a protic acid catalyst.

The term "glyoxal" is understood to mean both the free di-aldehyde form (i.e. OHC—CHO) and the hydrated forms (e.g. $(HO)_2HC$—CHO).

The term "glyoxalate" is understood to mean the glyoxalic acid or an alkaline salt of glyoxalic acid (such as OHC—COONa or OHC—COOK) or mixture thereof. The term "glyoxalate" is also understood to mean both the free aldehyde form (i.e. OHC—COOH) and the hydrated form (e.g. $(HO)_2HC$—COOH or $(HO)_2HC$—COONa).

For the sake of clarity, by the expression "an oligomeric composition", or the similar, it is meant the normal meaning understood by a person skilled in the art, i.e. a mixture of oligomers, as reaction product, and other optional components. In the simplest embodiment of the invention said optional embodiment can be, as non-limiting examples, water and/or unreacted reagent of the process (e.g. the acid catalyst). By "oligomer" it is meant a compound which is not itself a macropolymer, as is a resin, but rather a small size molecule comprising between about 4 to 100, or even preferably 30, units derived from the monomeric constituents.

According to a particular embodiment of the present invention, the invention's oligomers possess a molecular weight (MW) comprised between about 200 g/mol and 2500 g/mol. In still another aspect of the invention, said MW is comprised between about 220 g/mol and 1200 g/mol.

According to any one of the above embodiments of the present invention, as polyamine component it is used a mixture of melamine and at least one $C_{1-4}$ compound comprising two $NH_2$ functional groups. According to any one of the above embodiments of the present invention, said compound is a $C_{1-2}$ compound comprising two $NH_2$ functional groups. For the sake of clarity, by the expression "$C_{1-4}$ compound comprising two $NH_2$ functional groups", or the similar, it is meant a $C_{1-4}$ hydrocarbon compound comprising two $NH_2$ functional groups, and additionally said compound may optionally comprise from one to three nitrogen and/or oxygen atoms. In particular said compound is a $C_{1-2}$ compound comprising two $NH_2$ functional groups and a carbonyl or a 1,2,4-triazole functional group. Non-limiting examples of said $C_{1-4}$ compound comprising two $NH_2$ functional groups (diamino compound) can be urea, 1H-1,2,4-triazole-3,5-diamine and mixtures thereof.

According to any one of the above embodiments of the present invention, it can be used mixtures with a molar ratio melamine/diamino compound comprised between about 4/1 and 1/4, or even comprised between about 3.5/1 and 1/3.5, or alternatively between about 2/1 and 1/3, or alternatively between about 1.3/1 and 1/3. In the case where the diamino compound is 1H-1,2,4-triazole-3,5-diamine, one may also mention molar ratio melamine/1H-1,2,4-triazole-3,5-diamine comprised between about 1.5/1 and 1/1.5.

For the sake of clarity, by the expression "$C_{4-6}$ 2,2-dialkoxyethanal" it is meant a 2,2-dialkoxyethanal having in total from 4 to 6 carbon atoms. According to an embodiment of the present invention, said $C_{4-6}$ 2,2-dialkoxyethanal can be 2,2-dimethoxy-ethanal, 2,2-diethoxy-ethanal and mixtures thereof.

According to any one of the above embodiments of the present invention, said aldehyde component has a molar ratio glyoxal/2,2-dialkoxy-ethanal comprised between about 3/1 and 7/1, or even comprised between about 2.2/1 and 6.5/1, or even comprised between about 1.4/1 and 6.5/1. One may also mention that in the case where the diamino compound is urea, then said glyoxal/2,2-dialkoxy-ethanal may advantageously be comprised between about 3/1 and 6.1/1. One may also mention that in the case where the diamino compound is 1H-1,2,4-triazole-3,5-diamine, then said glyoxal/2,2-dialkoxy-ethanal may advantageously be comprised between about 1.4/1 and 2.2/1.

The aldehyde component may also include (as optional constituent) a glyoxalate. According to any one of the above embodiments of the present invention, when present, said glyoxalate is present in amounts such that molar ratio glyoxal/glyoxalate is comprised between about 4/1 and 1/1, or even comprised between about 3.5/1 and 2/1. According to any one of the above embodiments of the present invention, said glyoxalate is present and within amounts such as stated in the ratio mentioned above, in particular when the diamino compound is 1H-1,2,4-triazole-3,5-diamine.

According to any one of the above embodiments of the present invention, the said polyamine component and the aldehyde component are admixed in a ratio such that the molar ratio of total amine functional group/total free aldehyde functional group (also referred as $(NH_2)_{tot}/(CHO)_{tot}$) is comprised between about 2/1 and 1/2, or even comprised between about 1.5/1 and 1/1.5, or alternatively between about 1.2/1 and 1/1.2. For the purpose of clarity, a melamine accounts for 3 amine functional group and the diamino compound, e.g. urea, for 2. Similarly glyoxal accounts for 2 free aldehyde functional groups and the $C_{4-6}$ 2,2-dialkoxy-ethanal or the glyoxalate accounts for 1 free aldehyde functional group.

As a person skilled in the art understand and knows, said protic acid is a catalyst or initiator of the oligomerisation, and therefore said protic acid may react also with the other components and becoming, at least partially, part of the oligomers formed. According to any one of the above embodiments of the present invention, said protic acid catalyst is selected amongst mineral acids, $C_{1-6}$ mono or dicarboxylic acids and mixtures thereof. Non-limiting examples of such acids are phosphoric, nitric, sulfuric or hydrochloric acids, or acetic, formic, oxalic or glyoxilic acids. More specifically, said acid catalyst is selected amongst formic acid, acetic, glyoxylic acid and, nitric acids and mixtures thereof.

According to any one of the above embodiments of the present invention, the oligomeric composition is obtained by reacting the various components in water and the oligomeric composition is obtained by a single step process wherein all reagents are mixed together or by a multistep process wherein the reagents are reacted together subsequently.

According to any one of the above embodiments of the present invention, the oligomer is obtained by a process where all the various components are reacted together in water, and the pH of the final reaction medium is preferably comprised between 6 and 8.

According to any one of the above embodiments of the present invention, the oligomer is obtained by a two-step process. In a first step, the polyamine component is reacted with the aldehyde component in an aqueous medium, at a basic pH. Then in a second step, there is added to the reaction medium the acid catalyst, so as to work at an acidic pH.

According to any one of the above embodiments of the present invention, the pH of said first step can be comprised between about 7 and 10, or even between about 8.5 and 9.5. In still another aspect of the invention, the temperature of reaction of the first step can be comprised between about 20° C. and 80° C., or even between about 40° C. and 80° C.

In still another aspect of the invention, said first step can be carried out for about 0.1 hour to about 4 hours (reaction time). However, more specifically, the reaction time of said first step depends on the temperature of the reaction, and its pH and can be comprised, for example, between about 1 hour to about 4 hours, for a temperature comprised between about 40° C. and about 80° C. and a pH between about 8 and about 10. Alternatively said reaction time can be comprised, for example, between about 0.5 hour to about 2 hours, for a temperature comprised between about 50° C. and about 80° C. and a pH between about 7 and about 9.5.

The pH of said first step can be typically set up by adding to the reaction medium an adequate amount of potassium or sodium hydroxide.

According to any one of the above embodiments of the present invention, the said acid catalyst is added to the reaction mixture of the first step in an amount sufficient to acidify the latter. The pH of said second step can be comprised between about 4.0 and 6, or even between about 4.5 and 5.5. In still another aspect of the invention, the temperature of reaction of the first step can be comprised between about 40° C. and 100° C., or even between about 50° C. and 90° C.

In still another aspect of the invention, said second step can be carried out for about 0.5 hour to about 4 hours (reaction time). However, more specifically, the reaction time of said first step depends on the temperature of the reaction, and its pH and can be comprised, for example, between about 1 hour to about 2.5 hours, for a temperature comprised between about 50° C. and about 80° C. and a pH between about 4.5 and about 5.5. Alternatively said reaction time can be comprised, for example, between about 0.5 hour to about 4 hours, for a temperature comprised between about 50° C. and about 80° C. and a pH between about 4.5 and about 5.5.

As can be noticed, the result of such process is an aqueous solution comprising the invention oligomeric composition. Typically, the aqueous solution comprises between about 30% and 70% of oligomeric composition (solid content), percentage being expressed on a w/w basis relative to the total weight of the solution.

Said aqueous solution can be used directly for the process of preparation of the microcapsules, as described further below, or can be dried to provide the oligomeric composition.

The present invention's oligomeric composition differs, inter alia, from prior art oligomers by the use in its preparation of glyoxal, and in particular of a specific mixture of glyoxal and $C_{4-6}$ dialkoxyethanal. Without being bound by theory, it is believed that the specific use of said aldehyde component provides oligomers with free aldehyde or free OH groups (not available when using for instance only a 2,2-dialkoxy-ethanal, as aldehyde). Said free OH groups are expected to allow a better cross-linking during the formation of the microcapsule shell, translating into an improved stability and performance of core-shell microcapsules obtained using such oligomers, as shown further below.

Therefore, a second object of the present invention is a process for obtaining the above microcapsules using said oligomeric composition. In other words, a process for the preparation of a core-shell microcapsule, said process comprising the steps of:

1) preparing an oil-in-water dispersion, wherein the droplet size is comprised between 1 and 600 µm, and comprising at least an oligomeric composition as defined above;
2) optionally adding to the dispersion a $C_{1-4}$ compound comprising two $NH_2$ functional groups;
3) heating said dispersion;
4) cooling said dispersion; and
5) optionally drying the final dispersion to obtain the dried core-shell microcapsule.

For the sake of clarity, by the expression "core-shell microcapsule", or the similar, in the present invention it is meant that the capsule has a size in the micron range (e.g. a mean diameter comprised between about 1 and 600 µm) and comprises an external solid oligomers-based shell or wall and an internal continuous oil phase enclosed by the external shell. In other words bodies like coacervates or extrudates (i.e. porous solid phases containing droplets of a liquid) are not part of the invention. According to an embodiment of the invention, the size of said microcapsules, and consequently of the droplet size in step 1), is comprised between about 5 and 200 µm.

The dispersion in step 1) comprises at least an oligomeric composition of the invention as well as an oil. Said dispersion, as well known in the art, may also comprise as optional components at least a polyol and/or at least a stabilizer.

For the sake of clarity, by the expression "dispersion", in the present invention it is meant a system in which particles are dispersed in a continuous phase of a different composition and specifically includes a suspension or an emulsions.

According to any one of the above embodiments of the present invention, the dispersion comprises between about 1% and 10% of oligomeric composition, percentage being expressed on a w/w basis relative to the total weight of the dispersion. In still another aspect of the invention, the dispersion comprises between about 1% and 5% of oligomeric composition. In general the amount of oligomeric composition present in the dispersion can also be defined as being comprised between 5% and 15% of oligomeric composition on a w/w basis relative to the total weight of oil added in the dispersion.

According to any one of the above embodiments of the present invention, the dispersion comprises between about 10% and 50% of oil, percentage being expressed on a w/w basis relative to the total weight of the dispersion. In still another aspect of the invention, the dispersion comprises between about 20% and 40% of oil.

By "oil" we mean here an organic phase that is a liquid at about 20° C. and which will be in the core of the core-shell capsules. According to any one of the above embodiments of the present invention, said oil can be selected amongst a perfume, insecticide, malodor counteracting substance, fungicide, insect repellant, and the mixtures thereof.

According to any one of the above embodiments of the present invention, said oil is a perfume. Said perfume can be in the form of a pure perfuming ingredient or of a perfuming composition.

By "perfuming composition" it is meant here the normal meaning of the art, i.e. a composition comprising several perfuming ingredients and optionally at least one suitable solvent and/or at least one perfumery adjuvant.

By "perfuming ingredient" or "perfuming co-ingredient" it is meant here a compound, which is used in a perfuming preparation or a composition to impart a hedonic effect. In other words such a co-ingredient, to be considered as being a perfuming one, must be recognized by a person skilled in the art as being able to impart or modify in a positive or pleasant way the odor of a composition, and not just as having an odor.

The nature and type of the perfuming co-ingredients present in the base do not warrant a more detailed description here, which in any case would not be exhaustive, the skilled person being able to select them on the basis of his general knowledge and according to intended use or application and the desired organoleptic effect. In general terms, these perfuming co-ingredients belong to chemical classes as varied as alcohols, lactones, aldehydes, ketones, esters, ethers, acetates, nitriles, terpenoids, nitrogenous or sulphurous heterocyclic compounds and essential oils, and said perfuming co-ingredients can be of natural or synthetic origin. Many of these co-ingredients are in any case listed in reference texts such as the book by S. Arctander, Perfume and Flavor Chemicals, 1969, Montclair, N.J., USA, or its more recent versions, or in other works of a similar nature, as well as in the abundant patent literature in the field of perfumery. It is also understood that said co-ingredients may also be compounds known to release in a controlled manner various types of perfuming compounds.

By "suitable solvent" we mean here a material which is practically neutral from a perfumery point of view, i.e. that does not significantly alter the organoleptic properties of perfuming ingredients and is generally not miscible with water, i.e. possesses a solubility in water below 10%, or even below 5%. Say solvent is in general a solvent commonly used in perfumery, such as for example dipropyleneglycol, diethyl phthalate, isopropyl myristate, benzyl benzoate, 2-(2-ethoxyethoxy)-1-ethanol or ethyl citrate, limonene or other terpenes, isoparaffins such as those known under the trademark Isopar® (origin: Exxon Chemical) or glycol ethers and glycol ether esters such as those known under the trademark Dowanol® (origin: Dow Chemical Company).

By "perfumery adjuvant" we mean here an ingredient capable of imparting additional added benefit such as a color, a particular light resistance, chemical stability, etc. A detailed description of the nature and type of adjuvant commonly used in perfuming bases cannot be exhaustive, but it has to be mentioned that said ingredients are well known to a person skilled in the art.

According to an embodiment of the invention, the dispersion comprises also between about 0% and 5% of at least a stabilizer, percentage being expressed on a w/w basis relative to the total weight of the dispersion. In still another aspect of the invention, the dispersion comprises between about 0% and 2% of at least a stabilizer. In still another aspect of the invention, the dispersion comprises between about 0% and 0.5% of at least a stabilizer. In the case where the aldehyde component comprises also a glyoxalate, and in particular when the diamino compound is 1H-1,2,4-triazole-3,5-diamine, the dispersion comprises the amount of said stabilizer is 0% (no addition of stabilizer).

For the sake of clarity, in the present context by the expression "stabilizer", or the similar, it is meant the normal meaning understood by a person skilled in the art, i.e. a compound that is capable, or is added to, stabilize the system, e.g. to prevent aggregation or agglomeration of the microcapsules, for example in the application or during their preparation. The use of said stabilizer is standard knowledge of the person skilled in the art.

For the purpose of the present invention, said stabilizer can be a ionic or non-ionic surfactant or a colloidal stabilizer. The exact nature of such stabilizers is well known by a person skilled in the art. As non limiting examples one may cite the followings stabilizers: non-ionic polymers such as polyvinyl alcohol, cellulose derivatives such hydroxyethyl cellulose, polyethylene oxide, co-polymers of polyethylene oxide and polyethylene or polypropylene oxide, co-polymers alkyl acrylates and N-vinylpyrrolidone; ionic polymers such as co-polymers of acrylamide and acrylic acid (such as Alcapsol® 144 from Ciba), e.g. acid/acrylamide copolymers produced from monomer mixture of acrylic acid and acrylamide wherein the acrylic acid content is in the range of from 30 to 70%, acid anionic surfactant (such as sodium dodecyl sulfate), acrylic co-polymers bearing a sulfonate group (such as sodium poly(styrene sulfonate), and co-polymers of vinyl ethers and maleic anhydride.

According to any one of the above embodiments of the present invention, said stabilized is a ionic surfactant.

According to any one of the above embodiments of the present invention, the dispersion comprises also between about 0% and 10% of at least a polyol, percentage being expressed on a w/w basis relative to the total weight of the dispersion, or even comprised between about 0% and 2% of at least a polyol. In still another aspect of the invention, when the diamino compound is urea, said amount can be comprised between about 0.1% and 2% of at least a polyol. In still another aspect of the invention, when the diamino compound is 1H-1,2,4-triazole-3,5-diamine, said amount can be comprised between about 0% and 1.5% or 1% of at least a polyol.

For the sake of clarity, by the expression "polyol", or the similar, it is meant the normal meaning understood by a person skilled in the art, i.e. a compound comprising one or more alcohol functional groups and is generally used to help the reticulation/curing/deposition of the microcapsule's shell. The use of said polyol is standard knowledge of the person skilled in the art.

Said polyol may be selected from aromatic, aliphatic and polymeric polyols. As non-limiting examples one may cites aromatic polyol such as 3,5-dihydroxy toluene, resorcinol, xylenol, bisphenol, polyhydroxy naphthalene, polyphenol obtained by the degradation of cellulose; aliphatic polyol such as humic acids, 2,2,-dimethyl-1,3-propane diol, 1,1,1-tris-(hydroxymethyl)-propane, pentaerythritol, sorbitol or sugar derivatives and the similar; polymeric polyols such as celluloses or carboxymethyl cellulose derivatives such as alkaline salts of carboxymethyl cellulose (e.g. and in particular a sodium salt like Ambergum® 1221 (from HERCULES AQUALON)).

According to any one of the above embodiments of the present invention, said polyol is an aliphatic polymeric polyol such as a carboxymethyl ether cellulose derivative (such as, and in particular, Ambergum® 1221) or a chlorinated sugar such as sucralose.

Typical manners to form the dispersions of step 1) are known by a person skilled in the art, and are also described in the Examples herein below.

According to any one of the above embodiments of the present invention, the pH of said dispersion is set between 4 and 8. In still another aspect of the invention, the pH of said dispersion is comprised between 4.0 and 7.0. The dispersion may be stirred up to 24000 rpm to disperse oil in water (with mechanical stirrer, ultra Turrax or microwave).

According to any one of the above embodiments of the present invention, the thus obtained dispersion may be kept at room temperature or optionally heated at a temperature comprised between 30° C. and 70° C. In still another aspect of the invention, the temperature of said dispersion is comprised between 35° C. and 60° C. Said heating may be carried on for between about 0.5 hour and 6 hours. More specifically, the time of heating depends on the temperature and the pH of said emulsion or dispersion, and for example can be comprised between about 1 hour to about 2.5 hours, for a temperature comprised between about 35° C. and about 60° C. and a pH between about 4.5 and about 8.

According to the invention's process, it may be possible to add to the dispersion an appropriate amount of a $C_{1-4}$ compound comprising two $NH_2$ functional groups (diamino compound) as defined above. It is believed that said step helps the hardening of the microcapsule shell. Said step can be attractive in particular when there is used an oligomer wherein the $NH_{2tot}/CHO_{tot}$ ratio is close to the minimum of the range specified above.

According to any one of the above embodiments of the invention's process, said step 2) is performed (i.e. not optional). Said $C_{1-4}$ compound comprising two $NH_2$ functional groups (diamino compound) can be urea, 1H-1,2,4-triazole-3,5-diamine and mixtures thereof.

According to any one of the above embodiments of the invention, in step 2) there is added an amount of diamino compound comprised between about 5% and 100%, or even between about 10% and 80%, or alternatively between about 15% and 75%, percentage being expressed on a w/w basis relative to the total weight of the resin. It is clearly understood by a person skilled in the art, that only part of said added diamino compound will be incorporated into the microcapsule shell.

According to any one of the above embodiments of the invention, in step 3) the dispersion is heated at a temperature comprised between 60° C. and 100° C. In still another aspect of the invention, the temperature of said emulsion of dispersion is comprised between 70° C. and 90° C. Said thermal treatment may be carried on for between about 0.5 hour and 6 hours. More specifically, the time of heating depends on the temperature and the pH of said emulsion or dispersion, and for example can be comprised between about 1 hour to about 5 hours, for a temperature comprised between about 70° C. and about 80° C. and a pH between about 4.5 and about 8.

Step 4) of the invention's process is meant to stop the process of hardening of the shell of the thus obtained core-shell microcapsule, and can be performed by any known method. Typically, the dispersion can be cooled at temperatures comprised between about 10° and 30° C., in general to room temperature.

Said step 4) may optionally include a neutralization of the thus obtained dispersion at a pH comprised between pH between 6.5 and 7.5, for example by adding an appropriate amount of a base such as sodium hydroxide.

As noticed above, the result of such process is an aqueous dispersion (or slurry) comprising the invention core-shell microcapsule. Typically, the aqueous slurry comprises between 10% and 50% of capsules, percentage being expressed on a w/w basis relative to the total weight of the slurry. According to any one of the above embodiments of the invention, the aqueous slurry comprises between 20% and 50% of capsules.

Said aqueous slurry can be used directly as perfuming ingredient, in particular for applications which are aqueous based, e.g. a softener or a liquid soap. Therefore another object of the present invention is an aqueous slurry comprising the invention's microcapsules, for example a slurry as obtained directly for the process of preparation of the microcapsules. Said slurry may further comprise some formulation aids, such as stabilizer or viscosity control agents, or even biocides or bactericides.

Alternatively, the slurry obtained by the process described above can be submitted to a drying, like spay drying, to provide the microcapsules as such, i.e. in a powdery form. It is understood that any standard method known by a person skilled in the art to perform such drying is also applicable.

For the reasons set above, another object of the present invention is a composition of matter as obtained, or obtainable, by the above-described process. It is understood by a person skilled in the art that said composition of matter comprises the core-shell microcapsules in the dry form or as a water-suspension.

According to any one of the above embodiments of the invention, said core-shell microcapsules are those obtained by using in the invention's process an oil-in water dispersion wherein the oil is a perfume oil and, said dispersion comprises at least an oligomeric composition as defined above;
at least a stabilizer, as defined above;
at least a polyol, as defined above; and
adding at least a $C_{1-4}$ compound comprising two $NH_2$ functional groups, as defined above (step 2 of the invention's process).

According to any one of the above embodiments of said core-shell microcapsules, the amount of the core of oil accounts typically between 40% and 98% of the total weight of the microcapsules (i.e. the weight of the dispersion minus the weight of water). In still another aspect of the invention, said core of oil accounts between 70% and 95%, or even between 80% and 90%, of the total weight of the microcapsules.

According to any one of the above embodiments of said core-shell microcapsules, the amount of the shell accounts typically between 2% and 60% of the total weight of the capsules. In still another aspect of the invention, said oligomers-based shell accounts between 5% and 30%, or even between 10% and 20%, of the total weight of the microcapsules.

According to any one of the above embodiments of said core-shell microcapsules, the amount of stabilizer is comprised between 5% and 15%, percentage being expressed on a w/w basis relative to the total weight of the shell (i.e. the solid content of the microcapsule in a dry form). In still another aspect of the invention, the amount of stabilizer is comprised between 7% and 13%, percentage being expressed on a w/w basis relative to the total weight of the shell.

According to any one of the above embodiments of said core-shell microcapsules, the amount of polyol is comprised between 1% and 5%, percentage being expressed on a w/w basis relative to the total weight of the shell. In still another aspect of the invention, the amount of polyol is comprised between 1.5% and 3%, percentage being expressed on a w/w basis relative to the total weight of the shell.

According to any one of the above embodiments of said core-shell microcapsules, the amount of $C_{1-4}$ compound comprising two $NH_2$ functional groups is comprised between 2% and 30%, percentage being expressed on a w/w basis relative to the total weight of the shell. In still another aspect of the invention, the amount of $C_{1-4}$ compound comprising two $NH_2$ functional groups is comprised between 5% and 20%, percentage being expressed on a w/w basis relative to the total weight of the shell.

According to any one of the above embodiments of said core-shell microcapsules, the amount of oligomeric composition (in a dry form, as a clear for a person skilled in the art) is comprised between 50% and 95%, percentage being expressed on a w/w basis relative to the total weight of the shell. In still another aspect of the invention, the amount of oligomers is comprised between 65% and 90%, percentage being expressed on a w/w basis relative to the total weight of the shell.

According to any one of the above embodiments of the invention, said core-shell microcapsules are those obtained by using in the invention's process an oil-in water dispersion wherein the oil is a perfume oil and comprising at least an oligomeric composition as defined above and comprising a glyoxalate;
optionally at least a polyol, as defined above;
and wherein there is added during the process also at least a $C_{1-4}$ compound comprising two $NH_2$ functional groups, as defined above (step 2 of the invention's process), i.e. a process providing microcapsules capsules comprising glyoxalate and not comprising a stabilizer.

As mentioned above, the invention concerns the use of an invention's microcapsule as perfuming ingredient. In other words, it concerns a method to confer, enhance, improve or modify the odor properties of a perfuming composition or of a perfumed article, which method comprises adding to said composition or article an effective amount of at least an invention's microcapsule. By "use of an invention's microcapsule" it has to be understood here also the use of any composition containing an invention's microcapsule and which can be advantageously employed in perfumery industry.

Said compositions, which in fact can be advantageously employed as perfuming ingredients, are also an object of the present invention.

Therefore, another object of the present invention is a perfuming composition comprising:

i) as perfuming ingredient, at least one invention's microcapsule, or a slurry containing said invention's microcapsule, as defined above;
ii) at least one ingredient selected from the group consisting of a liquid perfumery carrier and a perfumery base; and
iii) optionally at least one perfumery adjuvant.

By "liquid perfumery carrier" we mean here a liquid material which is practically neutral from a perfumery point of view, i.e. which does not significantly alter the organoleptic properties of perfuming ingredients.

As liquid perfumery carrier one may cite, as non-limiting examples, an emulsifying system, i.e. a solvent and a surfactant system, or a solvent commonly used in perfumery. A detailed description of the nature and type of solvents commonly used in perfumery cannot be exhaustive. However, one can cite as non-limiting example solvents such as dipropyleneglycol, diethyl phthalate, isopropyl myristate, benzyl benzoate, 2-(2-ethoxyethoxy)-1-ethanol or ethyl citrate, which are the most commonly used. For the compositions which comprise both a perfumery carrier and a perfumery base, other suitable perfumery carriers, than those previously specified, can be also ethanol, water/ethanol mixtures, limonene or other terpenes, isoparaffins such as those known under the trademark Isopar® (origin: Exxon Chemical) or glycol ethers and glycol ether esters such as those known under the trademark Dowanol® (origin: Dow Chemical Company).

By "perfumery base" we mean here a composition comprising at least one perfuming co-ingredient, as defined above. The expression "perfumery adjuvant" is as defined above.

An invention's composition consisting of at least one invention's microcapsule and at least one perfumery carrier represents a particular embodiment of the invention as well as a perfuming composition comprising at least one invention's microcapsule, at least one perfumery carrier, at least one perfumery base, and optionally at least one perfumery adjuvant.

It is useful to mention here that the possibility to have, in the compositions mentioned above, more than one invention's microcapsule is important as it enables the perfumer to prepare accords, perfumes, possessing the odor tonality of various compounds of the invention, creating thus new tools for his work.

Furthermore, the invention's core-shell microcapsules can also be advantageously used in all the fields of modern perfumery, i.e. fine or functional perfumery, to positively impart or modify the odor of a consumer product into which said invention's microcapsules are added. Consequently, a perfuming consumer product which comprises:

i) as perfuming ingredient, at least one invention's microcapsule, as defined above; and
ii) a perfumery base;

is also an object of the present invention.

Said fine or functional perfumery may be a solid or a liquid product. According to a particular embodiment, liquid products are preferred.

For the sake of clarity, it has to be mentioned that, by "perfuming consumer product" it is meant a consumer product which is expected to deliver at least a perfuming effect, in other words it is a perfumed consumer product. For the sake of clarity, it has to be mentioned that, by "perfumery base" we mean here a consumer product which is compatible with perfuming ingredients and is expected to deliver a pleasant odor to the surface to which it is applied (e.g. skin, hair, textile, or home surface). In other words, a perfuming consumer product according to the invention comprises the functional formulation, as well as optionally additional benefit agents, corresponding to the desired consumer product, e.g. a detergent or an air freshener, and an olfactive effective amount of at least one invention's compound.

The nature and type of the constituents of the fine or functional perfumery base do not warrant a more detailed description here, which in any case would not be exhaustive, the skilled person being able to select them on the basis of his general knowledge and according to the nature and the desired effect of said product.

Non-limiting examples of suitable fine or functional perfumery base can be a perfume, such as a fine perfume, a cologne or an after-shave lotion; a fabric care product, such as a liquid or solid detergent, a fabric softener, a fabric refresher, an ironing water, a paper, or a bleach; a body-care product, such as a hair care product (e.g. a shampoo, a coloring preparation or a hair spray), a cosmetic preparation (e.g. a vanishing cream or a deodorant or antiperspirant), or a skin-care product (e.g. a perfumed soap, shower or bath mousse, oils or gel, or a hygiene product); an air care product, such as an air freshener or a "ready to use" powdered air freshener; or a home care product, such as a wipe, a dish detergent or hard-surface detergent.

According to an embodiment of the invention, the fine or functional perfumery base is in the form of a fabric, home, or hair care product, such as a fabric softener, a detergent or a shampoo.

Some of the above-mentioned consumer product bases may represent an aggressive medium for the invention's compound, so that it may be necessary to protect the latter from premature decomposition, for example by encapsulation or by chemically bounding it to another chemical which is suitable to release the invention's ingredient upon a suitable external stimulus, such as an enzyme, light, heat or a change of pH.

The proportions in which the compounds according to the invention can be incorporated into the various aforementioned articles or compositions vary within a wide range of values. These values are dependent on the nature of the article to be perfumed and on the desired organoleptic effect as well as the nature of the co-ingredients in a given base when the compounds according to the invention are mixed with perfuming co-ingredients, solvents or additives commonly used in the art.

For example, in the case of perfuming compositions, typical concentrations are in the order of 0.001% to 5% by weight, or even more, of the compounds of the invention based on the weight of the composition into which they are incorporated. Concentrations lower than these, such as in the order of 0.01% to 3% by weight, can be used when these compounds are incorporated into perfumed articles, percentage being relative to the weight of the article.

A BRIEF DESCRIPTION OF THE DRAWINGS

In all figures the vertical axis represents the weight loss in percentage of the slurry containing the microcapsules and as obtained by the process of preparation of the latter.

Figure 1B:
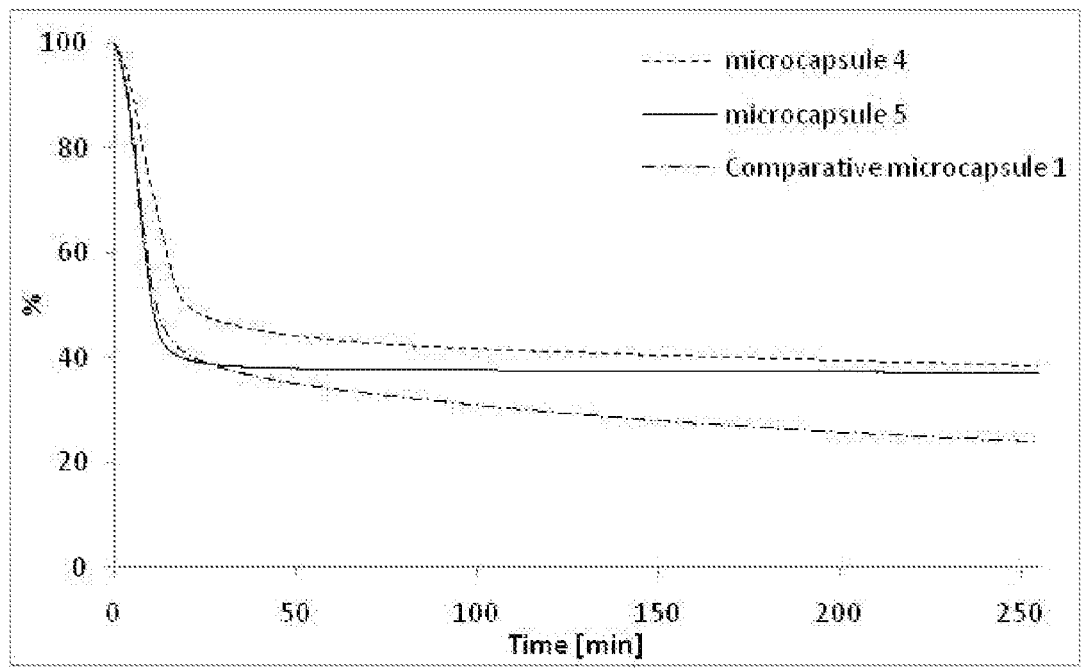

FIG. 1b/10: TGA analysis at 50° C. of a slurry obtained by the preparation of microcapsules 1-3 (oligomeric composition 1), versus Comparative microcapsule 1 (Comparative oligomers 3, prior art WO 2009/100553).

FIG. 1b/10: TGA analysis at 50° C. of a slurry obtained by the preparation of microcapsules 4 and 5 (oligomeric composition), versus Comparative microcapsule 1 (Comparative oligomers 3, prior art WO 2009/100553).

Figure 2A:
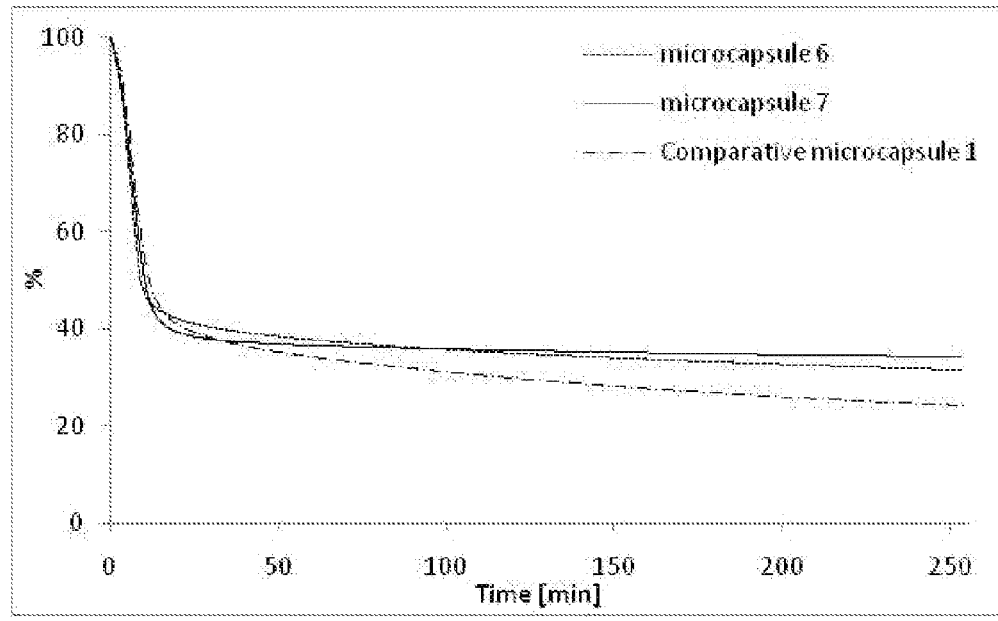

FIG. 2a/10: TGA analysis at 50° C. of a slurry obtained by the preparation of microcapsules 6 and 7 (oligomeric composition 3), versus Comparative microcapsule 1 (Comparative oligomers 3, prior art WO 2009/100553).

Figure 2B:
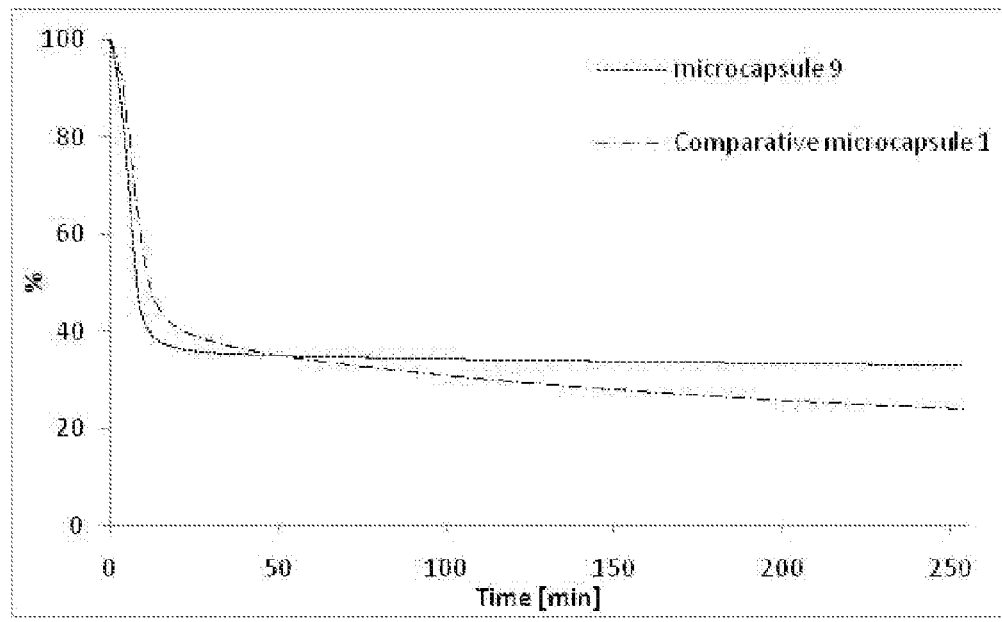

FIG. 2b/10: TGA analysis at 50° C. of a slurry obtained by the preparation of microcapsule 9 (oligomeric composition 4), versus Comparative microcapsule 1 (Comparative oligomers 3, prior art WO 2009/100553).

Figure 3A:
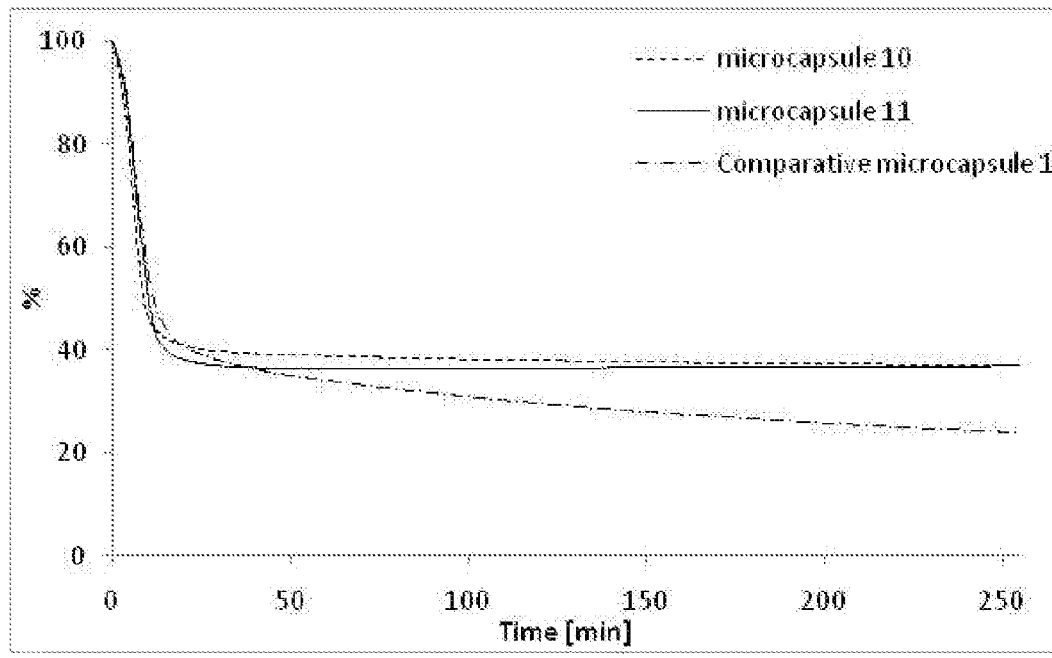

FIG. 3a/10: TGA analysis at 50° C. of a slurry obtained by the preparation of microcapsules 10 and 11 (oligomeric composition 5), versus Comparative microcapsule 1 (Comparative oligomers 3, prior art WO 2009/100553).

Figure 3B:
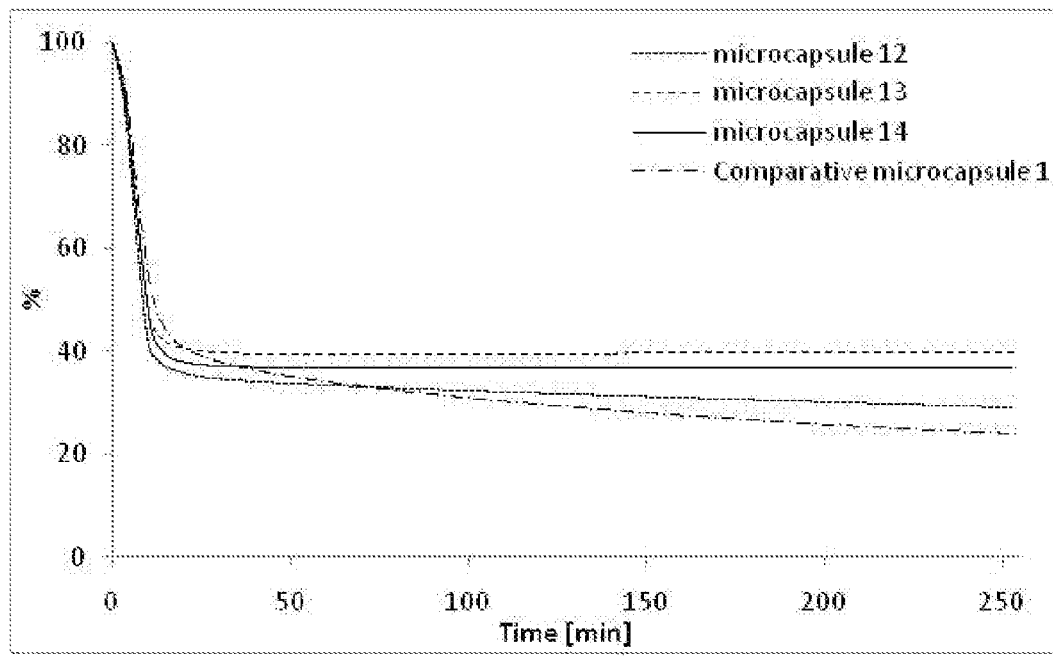

FIG. 3b/10: TGA analysis at 50° C. of a slurry obtained by the preparation of microcapsules 12 to 14 (oligomeric composition 6), versus Comparative microcapsule 1 (Comparative oligomers 3, prior art WO 2009/100553).

Figure 4A:
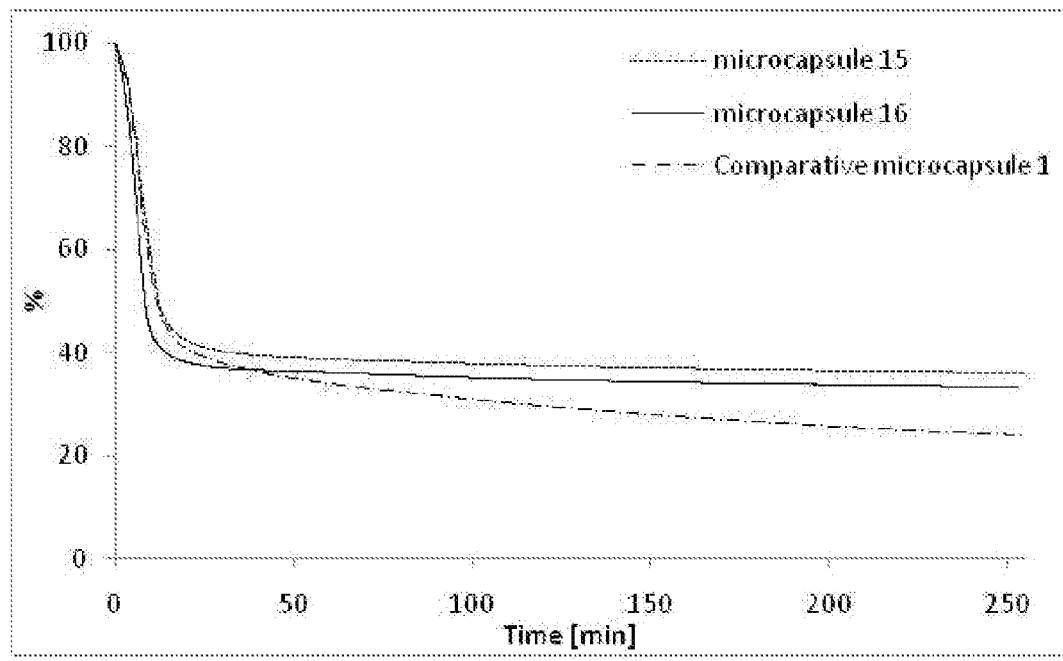

FIG. 4a/10: TGA analysis at 50° C. of a slurry obtained by the preparation of microcapsules 15 and 16 (oligomeric composition 7), versus Comparative microcapsule 1 (Comparative oligomers 3, prior art WO 2009/100553).

Figure 4B:
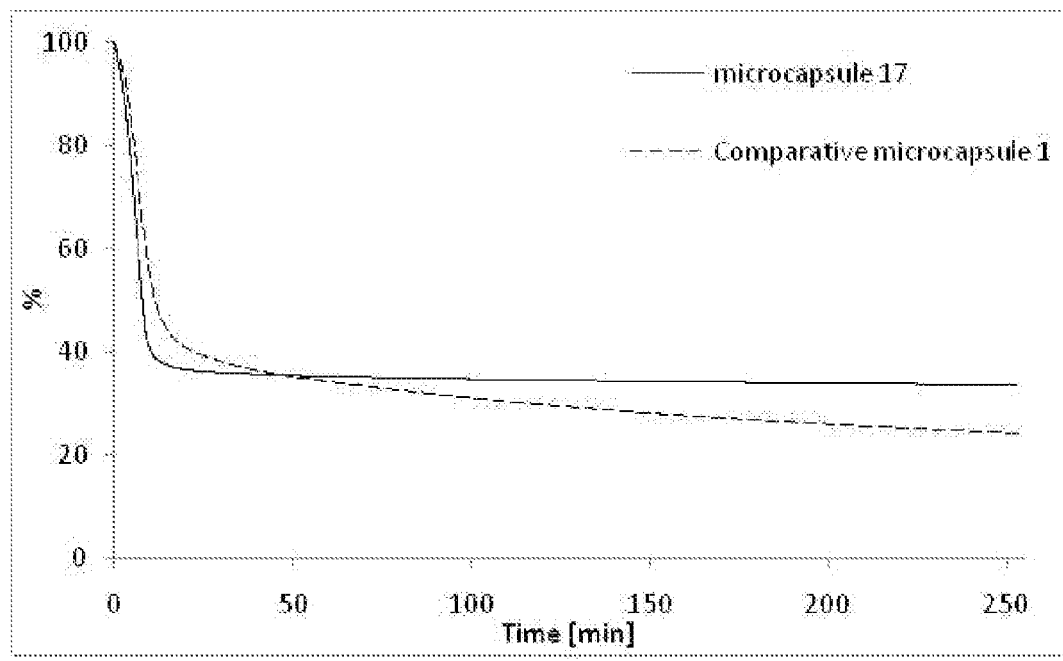

FIG. 4b/10: TGA analysis at 50° C. of a slurry obtained by the preparation of microcapsules 17 (oligomeric composition 6), versus Comparative microcapsule 1 (Comparative oligomers 3, prior art WO 2009/100553).

Figure 5A:
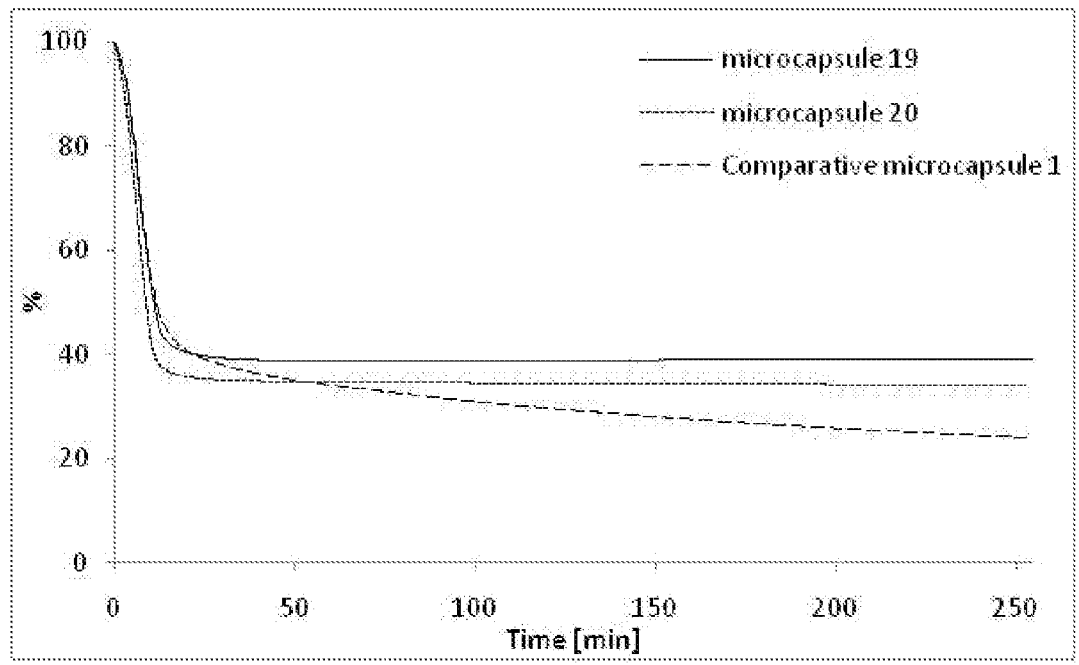

FIG. 5a/10: TGA analysis at 50° C. of a slurry obtained by the preparation of microcapsules 19 (oligomeric composition 8) and 20 (oligomeric composition 9), versus Comparative microcapsule 1 (Comparative oligomers 3, prior art WO 2009/100553).

Figure 5B:
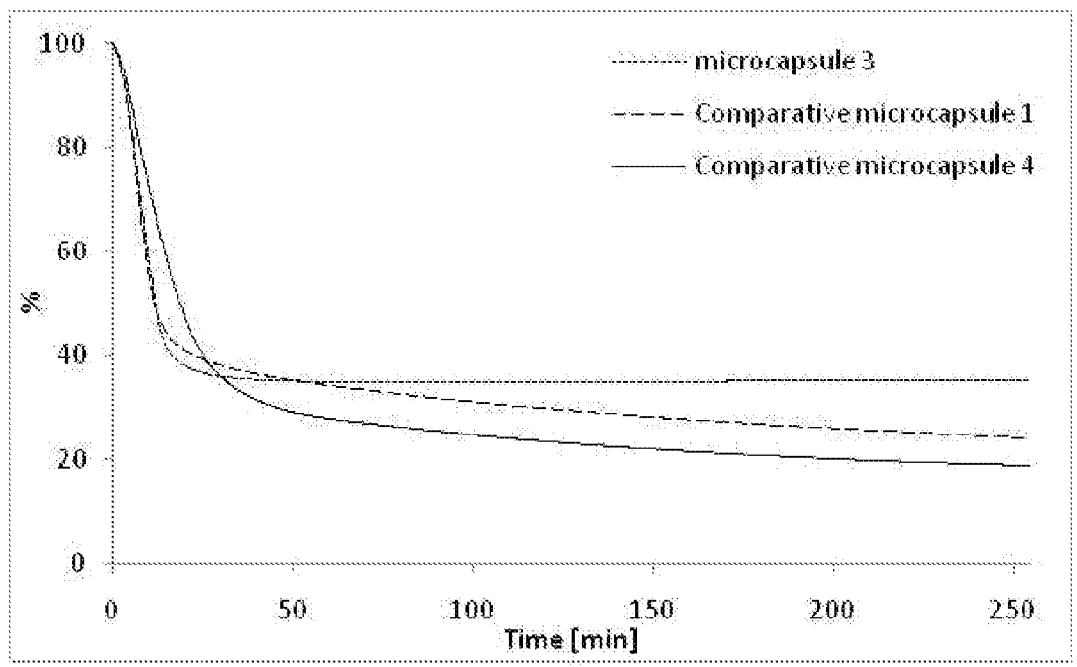

FIG. 5b/10: TGA analysis at 50° C. of a slurry obtained by the preparation of microcapsules 3 (oligomeric composition 1), versus Comparative microcapsule 1 (Comparative oligomers 3, prior art WO 2009/100553), and Comparative microcapsule 4 (Comparative oligomers 5).

Figure 6A:
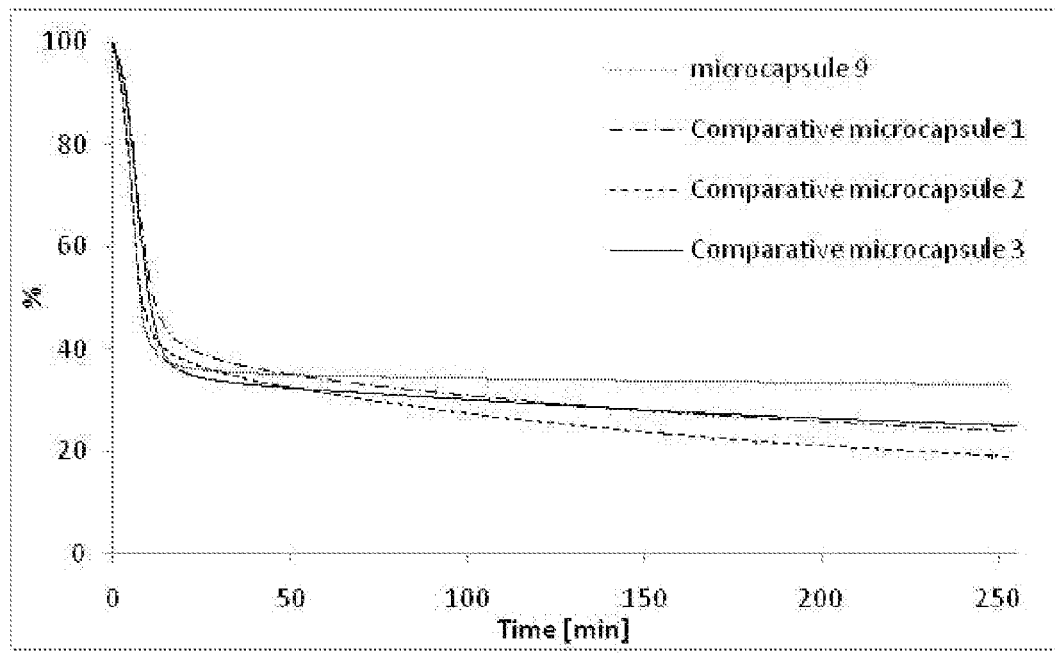

FIG. 6a/10: TGA analysis at 50° C. of a slurry obtained by the preparation of microcapsules 9 (oligomeric composition 4), versus Comparative microcapsule 1 (Comparative oligomers 3, prior art WO 2009/100553, no added urea in the process) and comparative microcapsules 2 and 3 (Comparative oligomers 3, prior art WO 2009/100553, with added urea in the process).

Figure 6B:
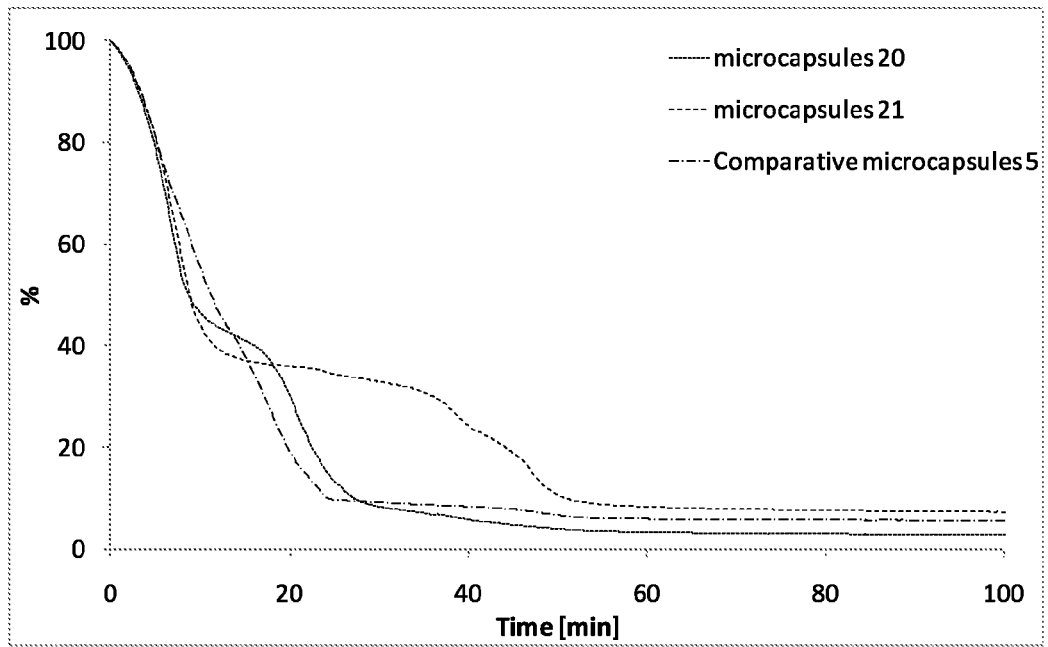

FIG. 6b/10: TGA analysis at 280° C. of a slurry obtained by the preparation of microcapsules 20 (oligomeric composition 12) and microcapsules 21 (oligomeric composition 12), versus Comparative microcapsule 5 (Comparative oligomers 3, prior art WO 2009/100553).

Figure 7A:
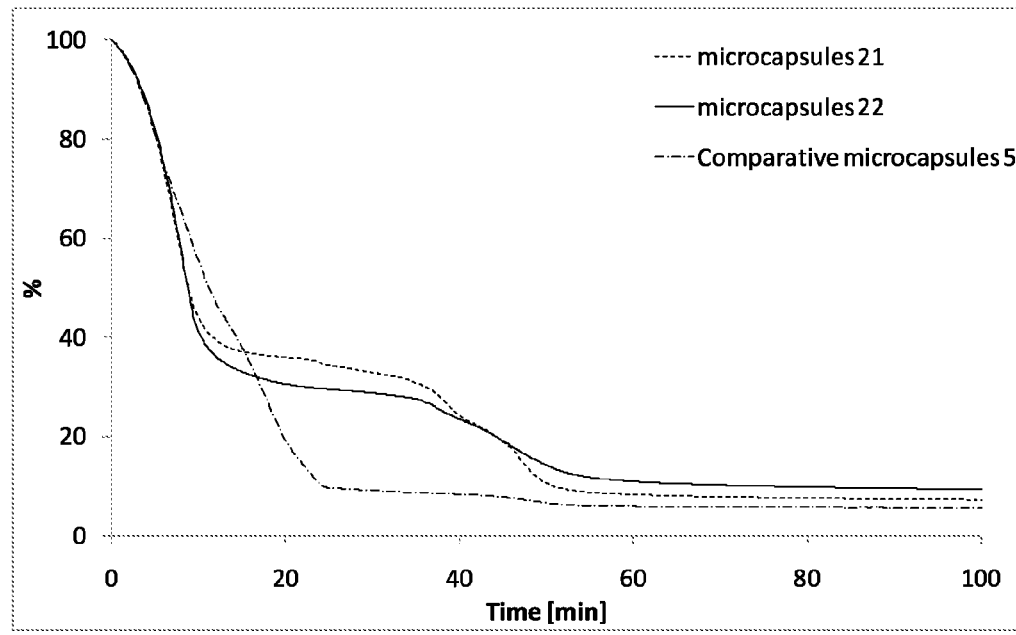

FIG. 7a/10: TGA analysis at 280° C. of a slurry obtained by the preparation of microcapsules 21 (oligomeric composition 12) and microcapsules 22 (oligomeric composition 12), versus Comparative microcapsule 5 (Comparative oligomers 3, prior art WO 2009/100553).

Figure 7B:
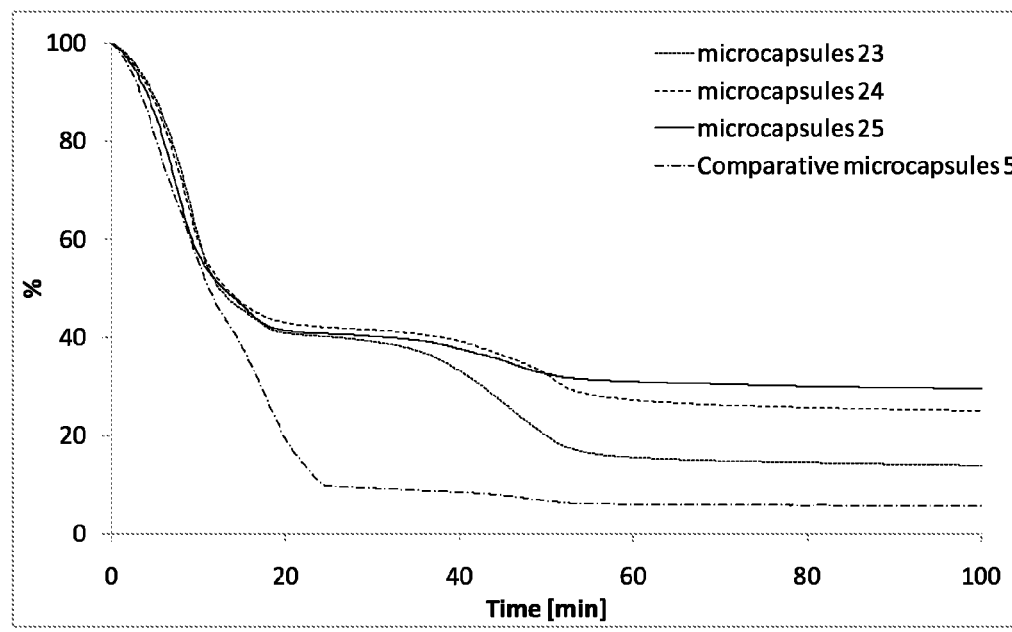

FIG. 7b/10: TGA analysis at 280° C. of a slurry obtained by the preparation of microcapsules 23 (oligomeric composition 12), microcapsules 24 (oligomeric composition 12, prepared at 70° C.) and microcapsules 24 (oligomeric composition 12, prepared at 80° C.), versus Comparative microcapsule 5 (Comparative oligomers 3, prior art WO 2009/100553).

Figure 8A:
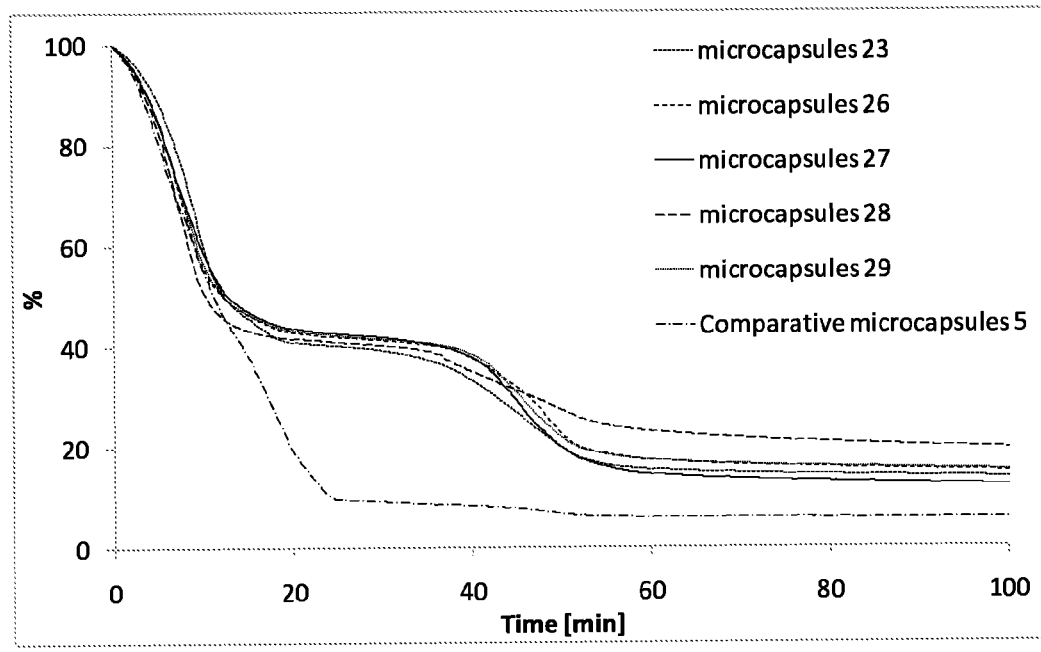

FIG. 8a/10: TGA analysis at 280° C. of a slurry obtained by the preparation of microcapsules 23 (oligomeric composition 12), microcapsules 26 (oligomeric composition 12), microcapsules 27 (oligomeric composition 12), microcapsules 28 (oligomeric composition 12) and microcapsules 29 (oligomeric composition 12), versus Comparative microcapsule 5 (Comparative oligomers 3, prior art WO 2009/100553).

Figure 8B:
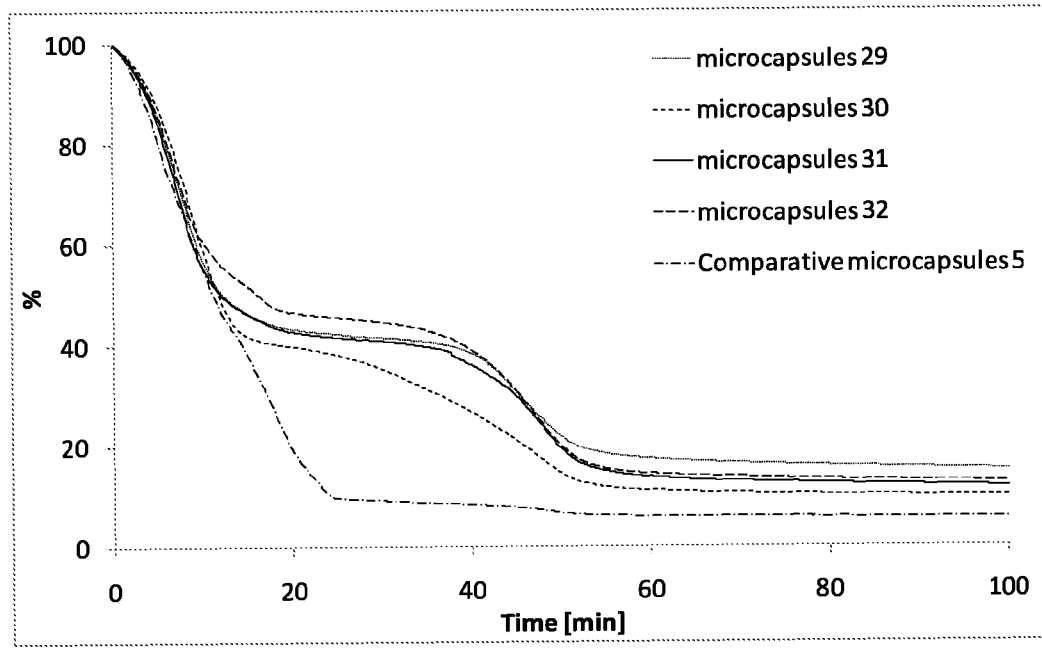

FIG. 8b/10: TGA analysis at 280° C. of a slurry obtained by the preparation of microcapsules 29 (oligomeric composition 12), microcapsules 30 (oligomeric composition 10), microcapsules 31 (oligomeric composition 11) and microcapsules 32 (oligomeric composition 6), versus Comparative microcapsule 5 (Comparative oligomers 3, prior art WO 2009/100553).

Figure 9A:
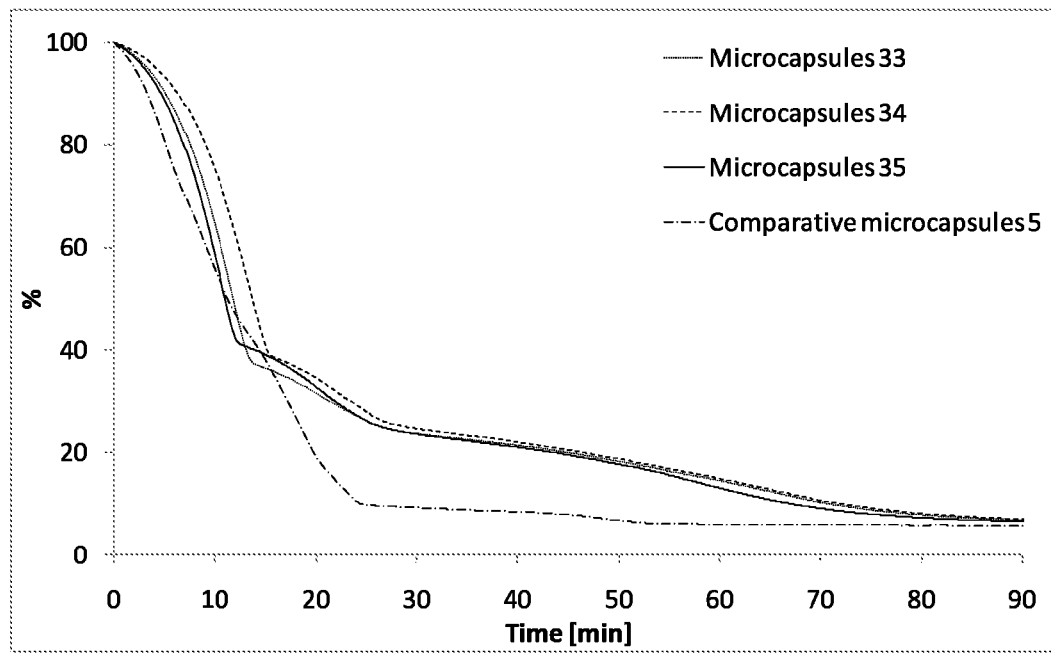

FIG. 9a/10: TGA analysis at 300° C. of a slurry obtained by the preparation of microcapsules 33 (oligomeric composition 13), microcapsules 34 (oligomeric composition 13), microcapsules 36 (oligomeric composition 13), and microcapsules 35 (oligomeric composition 13), versus Comparative microcapsule 5 (Comparative oligomers 3, prior art WO 2009/100553).

Figure 9B:
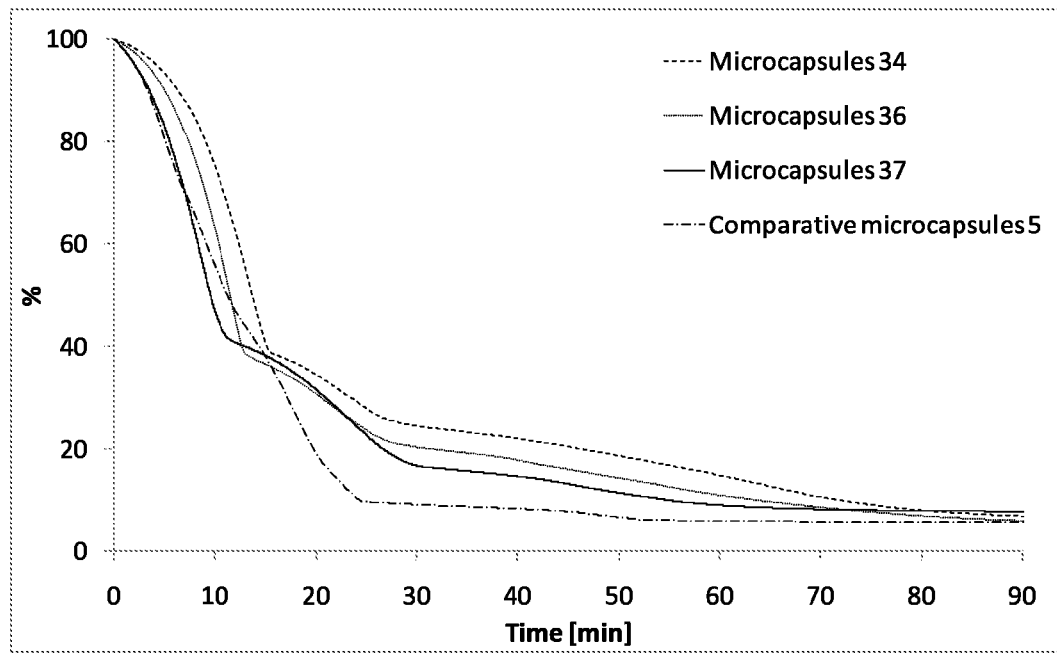

FIG. 9b/10: TGA analysis at 300° C. of a slurry obtained by the preparation of microcapsules 34 (oligomeric composition 13) and microcapsules 37 (oligomeric composition 13), versus Comparative microcapsule 5 (Comparative oligomers 3, prior art WO 2009/100553).

Figure 10A:
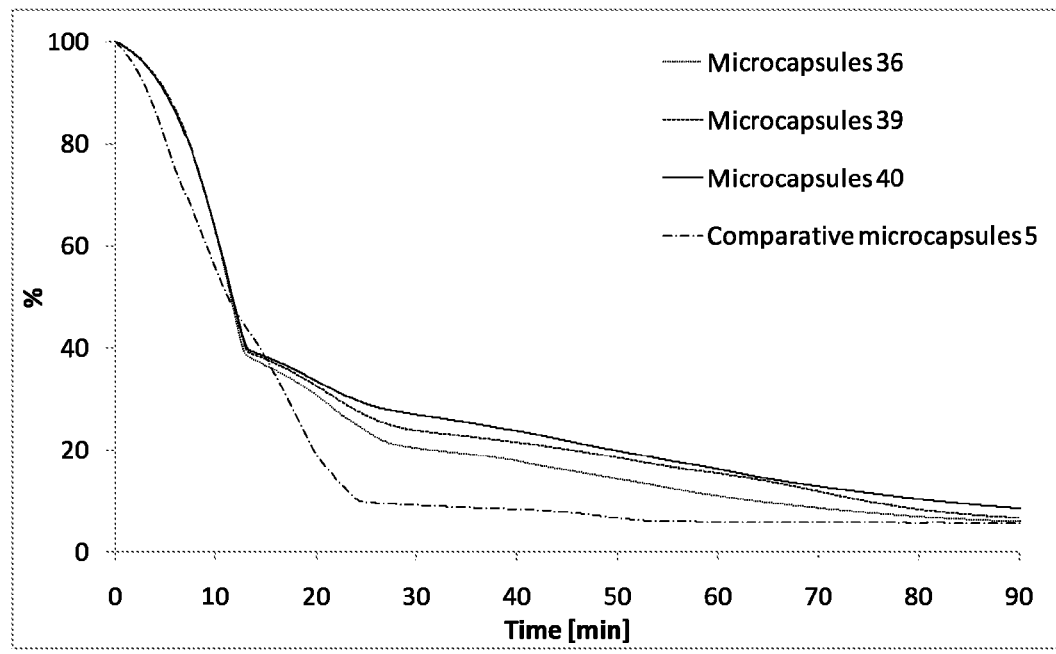

FIG. 10a/10: TGA analysis at 300° C. of a slurry obtained by the preparation of microcapsules 36 (oligomeric composition 13), microcapsules 39 (oligomeric composition 13) and microcapsules 40 (oligomeric composition 13), versus Comparative microcapsule 5 (Comparative oligomers 3, prior art WO 2009/100553).

Figure 10B:
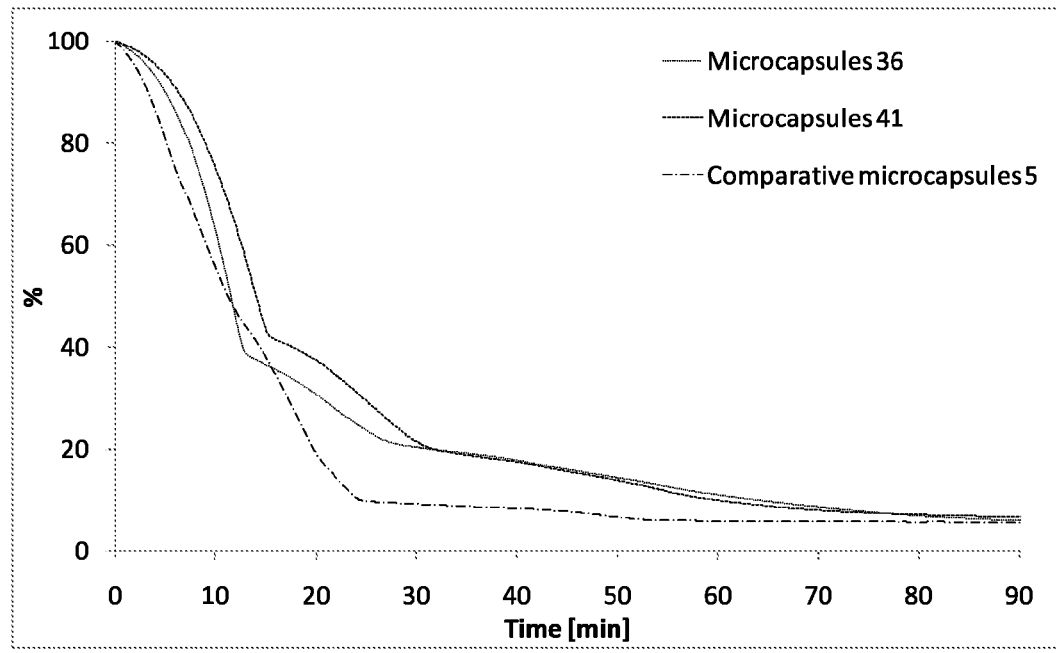

FIG. 10b/10: TGA analysis at 300° C. of a slurry obtained by the preparation of microcapsules 36 (oligomeric composition 13) and microcapsules 41 (oligomeric composition 14), versus Comparative microcapsule 5 (Comparative oligomers 3, prior art WO 2009/100553).

EXAMPLES

The invention will now be described in further detail by way of the following examples, wherein the abbreviations have the usual meaning in the art, the temperatures are indicated in degrees centigrade (° C.).

TGA: Solid content of resins was measured with a thermogravimetric analyser (Mettler-Toledo TGA/SDTA851$^e$) equipped with a microbalance (accuracy: 1 µg) and an accurate oven having an internal volume of 35 ml, under a constant nitrogen flow of 20 ml/min Resin (10 mg) was introduced in aluminium pan of 40 µl. The measurement started from 25° C. to 100° C. at 5° C./min, staid at 100° C. for 1 h, and finally to 200° C. at 10° C./min. The solid content was determined by doing the ratio between weight of sample (plateau) and the initial weight in the crucible.

Capsule performance was assessed at 50° C. (FIGS. 1a-6a), and 280° C. (FIGS. 6b-10b) or 300° C. (FIGS. 9a-10b) with a similar thermogravimetric analyser. Perfume evaporation was measured as a function of time. Microcapsules dispersion (10 mg) was introduced in alumina pan of 70 µl. The measurement at 50° C. started from 25° C. to 50° C. at 5° C./min, and then staid at 50° C. for 4 h. The measurement at 280° C. started from 25° C. to 280° C. at 5° C./min, and then staid at 280° C. for 1 h and 5 min. The measurement at 300° C. started from 25° C. to 300° C. at 5° C./min, and then staid at 300° C. for 1 h. A slower evaporation of the perfume oil with a long-lasting profile was related to a more stable capsule.

TOF-MS: The analysis of the resin compositions was carried out by liquid chromatography, with a TOF-MS detector (TOF High Resolution>10000, Agilent 1200 HPLC system Agilent G1969A MS TOF system composed of a Multimode source APCI+ESI) composed of a binary solvent manager (or pump G1312b), and an Auto sampler (g1329a). This TOF detector can analyze product having molecular weight up to 3000 g/mol. Analyses were carried out in formic acid aqueous solution at 0.1 wt % at RT without columns Method Standard: Water premix: Acid formic 0.1% (Biosolve n° 23244125 ULC/MSD lot 550361). HPLC: 0.5 ml/min, injection volume: 1 µl with welplate sampler (without column), temperature of thermostat: 60° C. (+/−0.1° C.). One blank run was performed between each sample.

MSD: Multi mode Electro spray (ESI)+APCI Pos LCMSD TOF High Resolution 3 ppm acq. Source: Mode Positive, Charging Voltage 2000 V, V cap 2500 V, Corona 4 µA, drying gas $N_2$, 5 l/min at 325° C., nebuliser 30 psig at 200° C. Fragmentor: 140 to 320 V. Scan range: 103 to 3000, online standard for mass adjustment.

SEC: Solutions of resins (0.5 wt %) were analyzed by size exclusion chromatography in formic acid 0.1 wt % and ammonium acetate 0.05M aqueous solution (mobile phase, pH=4.70). Analyses were carried out at 30° C. with a flow of 0.45 ml/min, by using a ThermoFinnigan Surveyor LC-Pump and Autosampler (20 µL injected). The column used was supplied by TOSOH BIOSCIENCE (TSKgel Super AW2500 6.0 mm ID, 15.0 cm L, polyvinyl resin). Molecular weights were measured by using ThermoFinnigan Surveyor UV/VIS detector and a SpectraSystem RI-150 refractive index detector (35° C.). Detectors were calibrated with standard poly (ethylene glycol) from 106 to 1982 g/mol.

Materials: 2,2-dimethoxyethanal (DME), oxalaldehyde (glyoxal, GY), and 2-oxoacetic acid (glyoxylic acid, AGY) were used as aqueous solutions at 60%, 40% and 50% w/w, respectively. 1,3,5-triazine-2,4,6-triamine (Melamine, M), urea and 1H-1,2,4-triazole-3,5-diamine (guanazole, T, purity=88.6%) were used as received. Ambergum® 1221 was used as a solution at 2% w/w in water. Alcapsol 144 was dissolved in water at 20% w/w. Sodium hydroxide (NaOH) was dissolved in water at 30% w/w. Nitric acid was used as a solution at 30% w/w in water. Formic acid (Aldrich, Switzerland) was used as received.

Example 1

Preparation of Oligomers According to the Invention

Oligomeric Composition 1:
In a round bottom flask of 250 ml, 1,3,5-triazine-2,4,6-triamine (melamine, 28 g, 222 mmol), urea (13.33 g, 222 mmol), 2,2-dimethoxyacetaldehyde (DME, 38.5 g, 222 mmol) and oxalaldehyde (glyoxal (GY), 64.4 g, 444 mmol) were dissolved in water (11 g, 611 mmol). The pH was adjusted with 0.51 g of sodium hydroxide aq. solution at 30 wt % (pH=8.89). The mixture was heated at 60° C. for 20 minutes. Then, nitric acid (23.56 g, 112 mmol) was added to fix pH at 4.52. The mixture was heated at 60° C. for 4 h. Solution was stored in the fridge (pH=4.04). Solid content=51 wt % (measured by TGA). Molecular weights (MW)=275 to 601 g/mol (measured by SEC).

TABLE 1

Ratio of the various starting materials

| Compound | m (g) | n (mol) | eq. | Ratio M/U | Ratio GY/DME | Ratio $NH_{2tot}/CHO_{tot}$ |
|---|---|---|---|---|---|---|
| Melamine | 28.00 | 222 | 1 | 1/1 | | 1/1 |
| Urea | 13.33 | 222 | 1 | | | |
| DME | 38.50 | 222 | 1 | | 2/1 | |
| GY | 64.40 | 444 | 2 | | | |

Oligomeric Composition 2:

In a round bottom flask of 25 ml, 1,3,5-triazine-2,4,6-triamine (melamine, 2.5 g, 19.9 mmol), urea (3.6 g, 59.5 mmol), 2,2-dimethoxyacetaldehyde (DME, 6.2 g, 35.7 mmol) and oxalaldehyde (GY, 10.4 g, 71.7 mmol) were dissolved in water (5 g, 277.8 mmol). The pH was adjusted with 0.57 g of sodium hydroxide aq. solution at 30 wt % (pH=9.31). The mixture was heated at 60° C. for 20 minutes. Then, nitric acid was added to fix pH at 4.60. The mixture was heated at 60° C. for 4 h. Solution was stored in the fridge (pH=4.73). Solid content=49.2 wt % (measured by TGA). MW=320 to 600 g/mol (measured by SEC).

TABLE 2

Ratio of the various starting materials

| Compound | m (g) | n (mol) | eq. | Ratio M/U | Ratio GY/DME | Ratio $NH_{2tot}/CHO_{tot}$ |
|---|---|---|---|---|---|---|
| Melamine | 2.5 | 19.9 | 1 | 1/3 | | 1/1 |
| Urea | 3.6 | 59.5 | 3 | | | |
| DME | 6.2 | 35.7 | 1.8 | | 2/1 | |
| GY | 10.4 | 71.7 | 3.6 | | | |

Oligomeric Composition 3:

In a round bottom flask of 25 ml, melamine (5.0 g, 39.7 mmol), urea (0.8 g, 13.1 mmol), 2,2-dimethoxyacetaldehyde (DME, 5.1 g, 29.1 mmol) and oxalaldehyde (GY, 8.4 g, 58.1 mmol) were dissolved in water (5 g, 277.8 mmol). The pH was adjusted with 0.39 g of sodium hydroxide aq. solution at 30 wt % (pH=9.02). The mixture was heated at 60° C. for 20 minutes. Then, nitric acid was added to fix pH at 4.40. The mixture was heated at 60° C. for 4 h. Solution was stored in the fridge (pH=4.72). Solid content is 50.5 wt % (measured by TGA). MW=305 to 586 g/mol (measured by SEC).

TABLE 3

Ratio of the various starting materials

| Compound | m (g) | n (mol) | eq. | Ratio M/U | Ratio GY/DME | Ratio $NH_{2tot}/CHO_{tot}$ |
|---|---|---|---|---|---|---|
| Melamine | 5.0 | 39.7 | 1 | 1/0.33 | | 1/1 |
| Urea | 0.8 | 13.1 | 0.33 | | | |
| DME | 5.1 | 29.1 | 0.73 | | 2/1 | |
| GY | 8.4 | 58.1 | 1.46 | | | |

Oligomeric Composition 4:

In a round bottom flask of 25 ml, melamine (6.0 g, 47.6 mmol), 2,2-dimethoxyacetaldehyde (DME, 4.95 g, 28.5 mmol) and oxalaldehyde (GY, 8.3 g, 57.0 mmol) were dissolved in water (5 g, 277.8 mmol). The pH was adjusted with 0.39 g of sodium hydroxide aq. solution at 30 wt % (pH=9.02). The mixture was heated at 60° C. for 20 minutes. Then, nitric acid was added to fix pH at 4.40. The mixture was heated at 60° C. for 4 h. Solution was stored in the fridge (pH=4.72). Solid content is 43.5 wt % (measured by TGA). MW=305 to 585 g/mol (measured by SEC).

TABLE 4

Ratio of the various starting materials

| Compound | m (g) | n (mol) | eq. | Ratio M/U | Ratio GY/DME | Ratio $NH_{2tot}/CHO_{tot}$ |
|---|---|---|---|---|---|---|
| Melamine | 6.0 | 47.6 | 1 | 1/0 | | 1/1 |
| DME | 4.95 | 28.5 | 0.6 | | 2/1 | |
| GY | 8.3 | 57.0 | 1.2 | | | |

Oligomeric Composition 5:

In a round bottom flask of 250 ml, 1,3,5-triazine-2,4,6-triamine (melamine, 28 g, 222 mmol), urea (13.33 g, 222 mmol), 2,2-dimethoxyacetaldehyde (DME, 38.5 g, 222 mmol) and oxalaldehyde (glyoxal (GY), 64.4 g, 444 mmol) were dissolved in water (11 g, 611 mmol). The pH was adjusted with 2.03 g of sodium hydroxide aq. solution at 30 wt % (pH=8.89). The mixture was heated at 60° C. for 10 minutes to give a white suspension which became more and more viscous (pH=7.15). Then, nitric acid (19 g, 90 mmol) was added to fix pH at 4.49. The mixture was heated at 60° C. for 4 h. Solution was stored in the fridge (pH=4.75). Solid content is 52.3 wt % (measured by TGA). MW=320 to 601 g/mol (measured by SEC).

TABLE 5

Ratio of the various starting materials

| Compound | m (g) | n (mol) | eq. | Ratio M/U | Ratio GY/DME | Ratio $NH_{2tot}/CHO_{tot}$ |
|---|---|---|---|---|---|---|
| Melamine | 28.00 | 222 | 1 | 1/1 | | 1/1 |
| Urea | 13.33 | 222 | 1 | | | |
| DME | 21.40 | 123.3 | 0.56 | | 4/1 | |
| GY | 71.60 | 493.3 | 2.22 | | | |

Oligomeric Composition 6:

In a round bottom flask of 250 ml, 1,3,5-triazine-2,4,6-triamine (melamine, 9.3 g, 74 mmol), urea (13.33 g, 222 mmol), 2,2-dimethoxyacetaldehyde (DME, 12.8 g, 74 mmol) and oxalaldehyde (glyoxal (GY), 42.9 g, 296 mmol) were dissolved in water (11 g, 611 mmol). The pH was adjusted with 1.3 g of sodium hydroxide aq. solution at 30 wt % (pH=9.03). The mixture was heated at 60° C. for 20 minutes. Then, nitric acid (19.0 g, 90 mmol) was added to fix pH at 4.48. The mixture was heated at 60° C. for 4 h. Solution was stored in the fridge (pH=4.57). Solid content is 49 wt % (measured by TGA). MW=320 to 601 g/mol (measured by SEC).

TABLE 6

Ratio of the various starting materials

| Compound | m (g) | n (mol) | eq. | Ratio M/U | Ratio GY/DME | Ratio $NH_{2tot}/CHO_{tot}$ |
|---|---|---|---|---|---|---|
| Melamine | 9.3 | 74 | 1 | 1/3 | | 1/1 |
| Urea | 13.3 | 222 | 3 | | | |
| DME | 12.8 | 74 | 1 | | 4/1 | |
| GY | 42.9 | 296 | 4 | | | |

Oligomeric Composition 7:

In a round bottom flask of 250 ml, 1,3,5-triazine-2,4,6-triamine (melamine, 12.6 g, 100 mmol), 2,2-dimethoxyacetaldehyde (DME, 5.8 g, 33.3 mmol) and oxalaldehyde (glyoxal (GY), 19.4 g, 133.3 mmol) were dissolved in water (11 g, 611 mmol). The pH was adjusted with 1.16 g of sodium hydroxide aq. solution at 30 wt % (pH=9.01). The mixture was heated at 60° C. for 5 minutes to give a white suspension which became more and more viscous. Then, nitric acid (18.6 g, 89 mmol) was added to fix pH at 0.67, followed by 4.5 g of sodium hydroxide aq. solution at 30 wt % (pH=4.43). The mixture was heated at 60° C. for 4 h. Solution was stored in the fridge (pH=4.10). Solid content is 41.4 wt % (measured by TGA). MW=334 to 615 g/mol (measured by SEC).

TABLE 7

Ratio of the various starting materials

| Compound | m (g) | n (mmol) | eq. | Ratio M/U | Ratio GY/DME | Ratio $NH_{2tot}/CHO_{tot}$ |
|---|---|---|---|---|---|---|
| Melamine | 12.6 | 100 | 1 | 1/0 | | 1/1 |
| DME | 5.8 | 33.3 | 0.33 | | 4/1 | |
| GY | 19.4 | 133.3 | 1.33 | | | |

Oligomeric Composition 8:

In a round bottom flask of 100 ml, 1,3,5-triazine-2,4,6-triamine (melamine, 3.0 g, 23.8 mmol), urea (4.3 g, 71.5 mmol), 2,2-dimethoxyacetaldehyde (DME, 2.9 g, 16.5 mmol) and oxalaldehyde (glyoxal (GY), 14.4 g, 99 mmol) were dissolved in water (5 g). The pH was adjusted with 0.8 g of sodium hydroxide aq. solution at 30 wt % (pH=9.45). The mixture was heated at 60° C. for 20 minutes. Then, nitric acid (1.2 g, 5.7 mmol) was added to fix pH at 4.67. The mixture was heated at 60° C. for 4 h. Solution was stored in the fridge (pH=4.64). Solid content=46.7 wt % (measured by TGA). MW=305 to 601 g/mol (measured by SEC).

TABLE 8

Ratio of the various starting materials

| Compound | m (g) | n (mmol) | eq. | Ratio M/U | Ratio GY/DME | Ratio $NH_{2tot}/CHO_{tot}$ |
|---|---|---|---|---|---|---|
| Melamine | 3.0 | 23.8 | 1 | 1/3 | | 1/1 |
| Urea | 4.3 | 71.5 | 3 | | | |
| DME | 2.9 | 16.5 | 0.69 | | 6/1 | |
| GY | 14.4 | 99 | 4.16 | | | |

Oligomeric Composition 9:

In a round bottom flask of 100 ml, 1,3,5-triazine-2,4,6-triamine (melamine, 3.0 g, 23.8 mmol), urea (4.3 g, 71.5 mmol), 2,2-dimethoxyacetaldehyde (DME, 1.8 g, 10.2 mmol) and oxalaldehyde (glyoxal (GY), 14.8 g, 102 mmol) were dissolved in water (4.5 g). The pH was adjusted with 1.1 g of sodium hydroxide aq. solution at 30 wt % (pH=9.46). The mixture was heated at 60° C. for 20 minutes. Then, nitric acid (2.7 g) was added to fix pH at 4.49. The mixture was heated at 60° C. for 4 h. Solution was stored in the fridge (pH=4.75). Solid content=45.8 wt % (measured by TGA). MW=305 to 601 g/mol (measured by SEC).

TABLE 9 ratio of the various starting materials

| Compound | m (g) | n (mmol) | eq. | Ratio M/U | Ratio GY/DME | Ratio $NH_{2tot}/CHO_{tot}$ |
|---|---|---|---|---|---|---|
| Melamine | 3.0 | 23.8 | 1 | 1/3 | | 1/1 |
| Urea | 4.3 | 71.4 | 3 | | | |
| DME | 1.8 | 10.2 | 0.43 | | 10/1 | |
| GY | 14.8 | 102 | 4.3 | | | |

Oligomeric Composition 10:

In a round bottom flask of 250 ml, melamine (0.93 g, 8.80 mmol), urea (0.87 g, 14.00 mmol), DME (0.63 g, 6.00 mmol) and GY (1.40 g, 24.20 mmol) were dissolved in water (10.00 g, 556.00 mmol). The pH was adjusted with 0.28 g of sodium hydroxide (pH=9.40). The mixture was heated at 60° C. for 20 minutes. Then, nitric acid (0.92 g, 4.30 mmol) was added to fix pH at 4.60. The resin can be use immediately to prepare the capsules.

TABLE 10

Ratio of the various starting materials

| Compound | m (g) | n (mol) | eq. | Ratio M/U | Ratio GY/DME | Ratio $NH_{2tot}/CHO_{tot}$ |
|---|---|---|---|---|---|---|
| Melamine | 0.93 | 8.8 | 1 | 1/1.6 | | 1/1 |
| Urea | 0.87 | 14.0 | 1.6 | | | |
| DME | 0.63 | 6.0 | 1 | | 4/1 | |
| GY | 1.40 | 24.2 | 4 | | | |

Oligomeric Composition 11:

In a round bottom flask of 250 ml, melamine (0.93 g, 8.80 mmol), urea (1.09 g, 17.60 mmol), DME (0.71 g, 6.80 mmol) and GY (1.58 g, 27.30 mmol) were dissolved in water (10.00 g, 556.00 mmol). The pH was adjusted with 0.34 g of sodium hydroxide (pH=9.45). The mixture was heated at 60° C. for 20 min. Then, nitric acid (0.91 g, 4.30 mmol) was added to fix pH at 4.61. The resin can be use immediately to prepare the capsules.

TABLE 11

Ratio of the various starting materials

| Compound | m (g) | n (mol) | eq. | Ratio M/U | Ratio GY/DME | Ratio $NH_{2tot}/CHO_{tot}$ |
|---|---|---|---|---|---|---|
| Melamine | 0.93 | 8.8 | 1 | 1/2 | | 1/1 |
| Urea | 1.09 | 17.6 | 2 | | | |
| DME | 0.71 | 6.8 | 1 | | 4/1 | |
| GY | 1.58 | 27.3 | 4 | | | |

Oligomeric Composition 12:

In a round bottom flask of 250 ml, melamine (4.67 g, 44.00 mmol), urea (6.69 g, 108.00 mmol), DME (4.02 g, 39 mmol) and GY (8.97 g, 155 mmol) were dissolved in water (5.50 g, 306.00 mmol). The pH was adjusted with 2.23 g of sodium hydroxide (pH=9.67). The mixture was heated at 60° C. for 20 minutes. Then, nitric acid (4.04 g, 19 mmol) was added to fix pH at 4.62. The mixture was heated at 60° C. for 4 h. Solution was stored in the fridge (pH=4.65). Solid content is 64% (measured by TGA).

TABLE 12

Ratio of the various starting materials

| Compound | m (g) | n (mol) | eq. | Ratio M/U | Ratio GY/DME | Ratio $NH_{2tot}/CHO_{tot}$ |
|---|---|---|---|---|---|---|
| Melamine | 4.67 | 44 | 1 | 1/2.45 | | 1/1 |
| Urea | 6.69 | 108 | 2.45 | | | |
| DME | 4.02 | 39 | 1 | | 4/1 | |
| GY | 8.97 | 155 | 4 | | | |

Oligomeric Composition 13:

In a round bottom flask of 50 ml, melamine (1.10 g, 8.78 mmol), DME (1.68 g, 9.69 mmol), AGY (0.72 g, 4.85 mmol) and GY (2.11 g, 14.54 mmol) were dissolved in water (1.90 g, 105.60 mmol). The pH was adjusted with 0.95 g of sodium hydroxide (pH=9.10). The mixture was heated at 45° C. for 25 min. Then, water (8.35 g, 463.90 mmol) was added and stirred 5 min Guanazole (0.98 g, 8.74 mmol), previously dissolved in water (22.50 mL) was added. The mixture was used immediately to make capsules.

TABLE 13

Ratio of the various starting materials

| Compound | m (g) | n (mol) | eq. | Ratio M/T | Ratio GY/DME/AGY | Ratio $NH_{2tot}/CHO_{tot}$ |
|---|---|---|---|---|---|---|
| Melamine | 1.1 | 8.78 | 1 | 1/1 | | 1/1 |
| Guanazole | 098 | 7.74 | 1 | | | |
| DME | 1.68 | 9.69 | 1.1 | | 3/2/1 | |
| GY | 2.11 | 14.55 | 1.66 | | | |
| AGY | 0.72 | 4.85 | 0.55 | | | |

Oligomeric Composition 14:

In a round bottom flask of 50 ml, melamine (1.10 g, 8.78 mmol), DME (1.68 g, 9.69 mmol), AGY (0.72 g, 4.85 mmol) and GY (2.11 g, 14.54 mmol) were dissolved in water (1.9 g, 105.60 mmol). The pH was adjusted with 0.95 g of sodium hydroxide (pH=9.10). The mixture was heated at 45° C. for 25 min. Then, water (8.35 g, 463.90 mmol) was added and stirred 5 min Guanazole (1.47 g, 13.08 mmol), dissolved in water (32.50 mL) was added. The mixture was used immediately to make capsules.

TABLE 14

Ratio of the various starting materials

| Compound | m (g) | n (mol) | eq. | Ratio M/T | Ratio GY/DME/AGY | Ratio $NH_{2tot}/CHO_{tot}$ |
|---|---|---|---|---|---|---|
| Melamine | 1.1 | 8.78 | 1 | 1/1.5 | | 1.2/1 |
| Guanazole | 098 | 7.74 | 1 | | | |
| DME | 1.68 | 9.69 | 1.1 | | 3/2/1 | |
| GY | 2.11 | 14.55 | 1.66 | | | |
| AGY | 0.72 | 4.85 | 0.55 | | | |

Example 2

Preparation of Comparative Oligomers, Out of the Scope of the Present Invention

Comparative Oligomers 1:

In a round bottom flask of 25 ml, urea (5.0 g, 83.0 mmol), 2,2-dimethoxyacetaldehyde (DME, 5.8 g, 33.3 mmol) and oxalaldehyde (GY, 9.7 g, 66.6 mmol) were dissolved in water (4 g, 222 mmol). The pH was adjusted with 0.39 g of sodium hydroxide aq. solution at 30 wt % (pH=9.02). The mixture was heated at 60° C. for 20 minutes. Then, nitric acid was added to fix pH at 4.40. The mixture was heated at 60° C. for 4 h. Solution was stored in the fridge (pH=4.72). Solid content is 48.2 wt % (measured by TGA). MW=334 to 601 g/mol (measured by SEC).

TABLE 1

Ratio of the various starting materials

| Compound | m (g) | n (mol) | eq. | Ratio M/U | Ratio GY/DME | Ratio $NH_{2tot}/CHO_{tot}$ |
|---|---|---|---|---|---|---|
| Urea | 5.0 | 83.0 | 1 | 0/1 | | 1/1 |
| DME | 5.8 | 33.3 | 0.4 | | 2/1 | |
| GY | 9.7 | 66.6 | 0.8 | | | |

Comparative Oligomers 2:

In a round bottom flask of 25 ml, urea (8.0 g, 133 mmol), 2,2-dimethoxyacetaldehyde (DME, 5.1 g, 29.6 mmol) and oxalaldehyde (glyoxal (GY), 17.1 g, 118.4 mmol) were dissolved in water (4 g, 222 mmol). The pH was adjusted with 5.33 g of sodium hydroxide aq. solution at 30 wt % (pH=9.05). The mixture was heated at 60° C. for 20 minutes. Then, nitric acid was added to fix pH at 4.65. The mixture was heated at 60° C. for 4 h. Solution was stored in the fridge (pH=4.73). Solid content is wt % (measured by TGA). MW=349 to 630 g/mol (measured by SEC).

TABLE 2

Ratio of the various starting materials

| Compound | m (g) | n (mol) | eq. | Ratio M/U | Ratio GY/DME | Ratio $NH_{2tot}/CHO_{tot}$ |
|---|---|---|---|---|---|---|
| Urea | 8 | 133 | 1 | 0/1 | | 1/1 |
| DME | 5.1 | 29.6 | 0.22 | | 4/1 | |
| GY | 17.1 | 118.4 | 0.89 | | | |

Comparative Oligomers 3: According to Prior Art WO 2009/100553

In a round bottom flask of 250 ml, 1,3,5-triazine-2,4,6-triamine (melamine, 11.2 g, 89 mmol) and 2,2-dimethoxyacetaldehyde (DME, 30.8 g, 178 mmol) were dissolved in water (3.7 g, 205 mmol). The pH was adjusted with 0.27 g of sodium hydroxide aq. solution at 30 wt % (pH=9.53). The mixture was heated at 60° C. for 2 h to give a solution. Then, formic acid (1.02 g, 22 mmol) was added to fix pH at 4.50. The mixture was heated at 60° C. for 4 h. Solution was stored in the fridge (pH=4.23). MW=350 g/mol (measured by SEC).

TABLE 3

Ratio of the various starting materials

| Compound | m (g) | n (mol) | eq. | Ratio $NH_{2tot}/CHO_{tot}$ |
|---|---|---|---|---|
| Melamine | 11.2 | 89 | 1 | 3/2 |
| DME | 30.8 | 178 | 2 | |

Comparative Oligomers 4:

In a round bottom flask of 100 ml, 1,3,5-triazine-2,4,6-triamine (melamine, 2.8 g, 22.2 mmol), urea (4.0 g, 66.6 mmol), and oxalaldehyde (glyoxal (GY), 14.5 g, 100 mmol) were dissolved in water (4 g, 205 mmol). The pH was adjusted with 1.78 g of sodium hydroxide aq. solution at 30 wt % (pH=9.06). The mixture was heated at 60° C. for 20 minutes.

Then, nitric acid (0.55 g, 2.6 mmol) was added to fix pH at 4.67. The mixture was heated at 60° C. for 4 h. Solution was stored in the fridge (pH=4.89). MW=305 to 601 g/mol (measured by SEC).

TABLE 4

Ratio of the various starting materials

| Compound | m (g) | n (mol) | eq. | Ratio M/U | Ratio $NH_{2tot}/CHO_{tot}$ |
|---|---|---|---|---|---|
| Melamine | 2.8 | 22.2 | 1 | 1/3 | 1/1 |
| Urea | 4.0 | 66.6 | 3 | | |
| GY | 14.5 | 100.0 | 4.5 | | |

Comparative Oligomers 5:

In a round bottom flask of 100 ml, 1,3,5-triazine-2,4,6-triamine (melamine, 5.0 g, 39.7 mmol), urea (2.4 g, 39.6 mmol), 2,2-dimethoxyacetaldehyde (DME, 22.9 g, 132 mmol) and oxalaldehyde (glyoxal (GY), 4.8 g, 33.1 mmol) were dissolved in water (4 g). The pH was adjusted with 0.83 g of sodium hydroxide aq. solution at 30 wt % (pH=9.24). The mixture was heated at 60° C. for 20 minutes. Then, nitric acid (1.91 g, 30.3 mmol) was added to fix pH at 4.56. The mixture was heated at 60° C. for 4 h. Solution was stored in the fridge (pH=4.95). Solid content=47.9 wt % (measured by TGA). MW=320 to 601 g/mol (measured by SEC).

TABLE 5

Ratio of the various starting materials

| Compound | m (g) | n (mol) | eq. | Ratio M/U | Ratio GY/DME | Ratio $NH_{2tot}/CHO_{tot}$ |
|---|---|---|---|---|---|---|
| Melamine | 5.0 | 39.7 | 1 | 1/1 | | 1/1 |
| Urea | 2.4 | 39.6 | 1 | | | |
| DME | 22.9 | 132.0 | 4 | | 1/4 | |
| GY | 4.8 | 33.1 | 1 | | | |

Example 3

Preparation of Core-Shell Microcapsules According to the Invention

Microcapsules 1:

In a 200 ml reactor, solutions of the polyol (Ambergum® 1221, 15.0 g, 2 wt % in water) and oligomeric composition 1 as directly obtained in Example 1 (4.5 g) were dissolved in water (30.0 g) and stirred for 30 minutes at RT (pH=4.55). Perfume oil (20.0 g, see Table below) was added and the reaction mixture was sheared with ultra turrax at 24000 rpm for 2 minutes. A solution of colloidal stabilizer was introduced (Alcapsol® 144, 20 wt % in water, 0.4 g, pH=4.73). The reaction mixture was heated at 40° C. for 1 h, then at 60° C. for 2 h, and finally at 75° C. for 3 h. The resulting slurry was cooled down (pH=4.79) and neutralized with a solution of sodium hydroxide (30 wt % in water, 0.24 g, pH=6.37).

TABLE

Perfume oil composition

| Raw material | Amount (g) |
|---|---|
| Romascone ® | 4.0 |
| Verdox ® | 4.0 |
| Dorisyl ® | 4.0 |
| Lilial ® | 4.0 |
| Hexyl Salicylate | 4.0 |

TABLE 1 w/w percentage of the various components introduced stepwise in the dispersion

| Raw material | Amount (g) | % (w/w) |
|---|---|---|
| 1. Ambergum ® 1221 (2% w/w in water) | 15.00 | 0.43 |
| 2. Oligomeric composition 1 (51% w/w in water) | 4.50 | 3.27 |
| 3. Demineralised water | 30.00 | To balance |
| 4. Perfume | 20.00 | 28.53 |
| 5. Alcapsol ® 144 (20% w/w in water) | 0.40 | 0.11 |
| 6. NaOH (30% w/w in water) | 0.24 | 0.09 |
| Total | 70.14 | 100 |

Microcapsules 2:

In a 200 ml reactor, solutions of Ambergum® 1221 (15.0 g, 2 wt % in water) and oligomeric composition 1 as directly obtained in Example 1 (4.5 g) were dissolved in water (30.0 g) and stirred for 30 minutes at RT (pH=4.53). Perfume oil (20.0 g, Table 2) was added and the reaction mixture was sheared with ultra turrax at 24000 rpm for 2 minutes. A solution of colloidal stabilizer was introduced (Alcapsol® 144, 20 wt % in water, 0.4 g, pH=4.72). The reaction mixture was heated at 40° C. for 1 h, and at 60° C. for 1 h. A solution of urea (50 wt %, 1.0 g) was introduced and reaction mixture was stirred at 60° C. for 1 h. Finally, mixture was heated at 75° C. for 3 h. The resulting slurry was cooled down (pH=4.87) and neutralized with a solution of sodium hydroxide (30 wt % in water, 0.23 g, pH=6.75).

TABLE 2 w/w percentage of the various components introduced stepwise in the dispersion

| Raw material | Amount (g) | % (w/w) |
|---|---|---|
| 1. Ambergum ® 1221 (2% w/w in water) | 15.00 | 0.42 |
| 2. Oligomeric composition 1 (51% w/w in water) | 4.50 | 3.22 |
| 3. Demineralised water | 30.00 | To balance |
| 4. Perfume oil | 20.00 | 28.12 |
| 5. Alcapsol ® 144 (20% w/w in water) | 0.40 | 0.11 |
| 6. Urea (50% w/w in water) | 1.00 | 0.70 |
| 7. NaOH (30% w/w in water) | 0.23 | 0.10 |
| Total | 71.13 | 100 |

Microcapsules 3:

In a 200 ml reactor, solutions of Ambergum® 1221 (30.0 g, 2 wt % in water) and oligomeric composition 1 as directly obtained in Example 1 (9.0 g) were dissolved in water (60.0 g) and stirred for 30 minutes at RT (pH=4.65). Perfume oil (40.0 g, Table 11) was added and the reaction mixture was sheared with ultra turrax at 24000 rpm for 2 minutes. A solution of colloidal stabilizer was introduced (Alcapsol® 144, 20 wt % in water, 0.8 g, pH=4.58). The reaction mixture was heated at 40° C. for 1 h, and at 60° C. for 1 h. A solution of urea (50 wt % in water, 4.0 g) was introduced at 60° C. and reaction mixture was stirred for 1 h. Finally, mixture was heated at 75°

C. for 3 h. The resulting slurry was cooled down (pH=4.76) and neutralized with a solution of sodium hydroxide (30 wt % in water, 0.47 g, pH=6.45).

TABLE 3 w/w percentage of the various components introduced stepwise in the dispersion

| Raw material | Amount (g) | % (w/w) |
|---|---|---|
| 1. Ambergum ® 1221 (2% w/w in water) | 30.00 | 0.42 |
| 2. Oligomeric composition 1 (51% w/w in water) | 9.00 | 3.18 |
| 3. Demineralised water | 60.00 | To balance |
| 4. Perfume oil | 40.00 | 27.72 |
| 5. Alcapsol ® 144 (20% w/w in water) | 0.80 | 0.11 |
| 6. Urea (50% w/w in water) | 4.00 | 1.39 |
| 7. NaOH (30% w/w in water) | 0.47 | 0.11 |
| Total | 144.27 | 100 |

Microcapsules 4:

The microcapsules were prepared as described for microcapsule 2, using oligomeric composition 2.

TABLE 4 w/w percentage of the various components introduced stepwise in the dispersion

| Raw material | Amount (g) | % (w/w) |
|---|---|---|
| 1. Ambergum ® 1221 (2% w/w in water) | 15.00 | 0.42 |
| 2. Oligomeric composition 2 (49.2% w/w in water) | 4.50 | 3.21 |
| 3. Demineralised water | 30.00 | To balance |
| 4. Perfume oil | 20.00 | 27.99 |
| 5. Alcapsol ® 144 (20% w/w in water) | 0.40 | 0.11 |
| 6. Urea (50% w/w in water) | 1.00 | 0.70 |
| 7. NaOH (30% w/w in water) | 0.15 | 0.06 |
| Total | 71.45 | 100 |

Microcapsules 5:

The microcapsules were prepared as described for microcapsule 3, using oligomeric composition 2.

TABLE 5 w/w percentage of the various components introduced stepwise in the dispersion

| Raw material | Amount (g) | % (w/w) |
|---|---|---|
| 1. Ambergum ® 1221 (2% w/w in water) | 15.00 | 0.42 |
| 2. Oligomeric composition 2 (49.2% w/w in water) | 4.50 | 3.07 |
| 3. Demineralised water | 30.00 | To balance |
| 4. New-mix | 20.00 | 27.69 |
| 5. Alcapsol ® 144 (20% w/w in water) | 0.40 | 0.11 |
| 6. Urea (50% w/w in water) | 2.00 | 1.38 |
| 7. NaOH (30% w/w in water) | 0.19 | 0.08 |
| Total | 72.09 | 100 |

Microcapsules 6:

The microcapsules were prepared as described for microcapsule 2, using oligomeric composition 3.

TABLE 6 w/w percentage of the various components introduced stepwise in the dispersion

| Raw material | Amount (g) | % (w/w) |
|---|---|---|
| 1. Ambergum ® 1221 (2% w/w in water) | 15.00 | 0.41 |
| 2. Oligomeric composition 3 (50.5% w/w in water) | 4.50 | 3.20 |
| 3. Demineralised water | 30.00 | To balance |
| 4. Perfume oil | 20.00 | 28.13 |
| 5. Alcapsol ® 144 (20%) | 0.40 | 0.11 |
| 6. Urea (50% w/w in water) | 1.00 | 0.70 |
| 7. NaOH (30% w/w in water) | 0.19 | 0.08 |
| Total | 71.09 | 100 |

Microcapsules 7:

The microcapsules were prepared as described for microcapsule 3, using oligomeric composition 3.

TABLE 7 w/w percentage of the various components introduced stepwise in the dispersion

| Raw material | Amount (g) | % (w/w) |
|---|---|---|
| 1. Ambergum ® 1221 (2% w/w in water) | 15.00 | 0.41 |
| 2. Oligomeric composition 3 (50.5% w/w in water) | 4.50 | 3.14 |
| 3. Demineralised water | 30.00 | To balance |
| 4. Perfume oil | 20.00 | 27.60 |
| 5. Alcapsol ® 144 (20% w/w in water) | 0.40 | 0.11 |
| 6. Urea (50% w/w in water) | 2.00 | 1.38 |
| 7. NaOH (30% w/w in water) | 0.17 | 0.07 |
| Total | 72.47 | 100 |

Microcapsules 8:

The microcapsules were prepared as described for microcapsule 1, using oligomeric composition 4.

TABLE 8 w/w percentage of the various components introduced stepwise in the dispersion

| Raw material | Amount (g) | % (w/w) |
|---|---|---|
| 1. Ambergum ® 1221 (2% w/w in water) | 15.00 | 0.42 |
| 2. Oligomeric composition 4 (43.5% w/w in water) | 4.50 | 2.78 |
| 3. Demineralised water | 30.00 | To balance |
| 4. Perfume oil | 20.00 | 28.37 |
| 5. Alcapsol ® 144 (20% w/w in water) | 0.40 | 0.11 |
| 6. NaOH (30% w/w in water) | 0.19 | 0.08 |
| Total | 70.49 | 100 |

Microcapsules 9:

The microcapsules were prepared as described for microcapsule 3, using oligomeric composition 4.

TABLE 9 w/w percentage of the various components introduced stepwise in the dispersion

| Raw material | Amount (g) | % (w/w) |
|---|---|---|
| 1. Ambergum ® 1221 (2% w/w in water) | 15.00 | 0.42 |
| 2. Oligomeric composition 4 (43.5% w/w in water) | 4.50 | 2.71 |
| 3. Demineralised water | 30.00 | To balance |

TABLE 9-continued w/w percentage of the various components introduced stepwise in the dispersion

| Raw material | Amount (g) | % (w/w) |
|---|---|---|
| 4. Perfume oil | 20.00 | 27.71 |
| 5. Alcapsol ® 144 (20%) | 0.40 | 0.11 |
| 6. Urea (50% w/w in water) | 2.00 | 1.39 |
| 7. NaOH (30% w/w in water) | 0.23 | 0.09 |
| Total | 72.13 | 100 |

Microcapsules 10:

The microcapsules were prepared as described for microcapsule 2, using oligomeric composition 5.

TABLE 10 w/w percentage of the various components introduced stepwise in the dispersion

| Raw material | Amount (g) | % (w/w) |
|---|---|---|
| 1. Ambergum ® 1221 (2% w/w in water) | 15.00 | 0.42 |
| 2. Oligomeric composition 5 (52.3% w/w in water) | 4.50 | 3.31 |
| 3. Demineralised water | 30.00 | To balance |
| 4. Perfume oil | 20.00 | 28.10 |
| 5. Alcapsol ® 144 (20% w/w in water) | 0.40 | 0.11 |
| 6. Urea (50% w/w in water) | 1.00 | 0.70 |
| 7. NaOH (30% w/w in water) | 0.28 | 0.12 |
| Total | 71.18 | 100 |

Microcapsules 11:

The microcapsules were prepared as described for microcapsule 3, using oligomeric composition 5.

TABLE 11 w/w percentage of the various components introduced stepwise in the dispersion

| Raw material | Amount (g) | % (w/w) |
|---|---|---|
| 1. Ambergum ® 1221 (2% w/w in water) | 15.00 | 0.42 |
| 2. Oligomeric composition 5 (52.3% w/w in water) | 4.50 | 3.26 |
| 3. Demineralised water | 30.00 | To balance |
| 4. Perfume oil | 20.00 | 27.69 |
| 5. Alcapsol ® 144 (20% w/w in water) | 0.40 | 0.11 |
| 6. Urea (50% w/w in water) | 2.00 | 1.38 |
| 7. NaOH (30% w/w in water) | 0.33 | 0.14 |
| Total | 72.23 | 100 |

Microcapsules 12:

The microcapsules were prepared as described for microcapsule 1, using oligomeric composition 6.

TABLE 12 w/w percentage of the various components introduced stepwise in the dispersion

| Raw material | Amount (g) | % (w/w) |
|---|---|---|
| 1. Ambergum ® 1221 (2% w/w in water) | 15.00 | 0.43 |
| 2. Oligomeric composition 6 (49% w/w in water) | 4.50 | 3.15 |
| 3. Demineralised water | 30.00 | To balance |
| 4. Perfume oil | 20.00 | 28.53 |

TABLE 12-continued w/w percentage of the various components introduced stepwise in the dispersion

| Raw material | Amount (g) | % (w/w) |
|---|---|---|
| 5. Alcapsol ® 144 (20% w/w in water) | 0.40 | 0.11 |
| 6. NaOH (30% w/w in water) | 0.21 | 0.09 |
| Total | 70.11 | 100 |

Microcapsules 13:

The microcapsules were prepared as described for microcapsule 2, using oligomeric composition 6.

TABLE 13 w/w percentage of the various components introduced stepwise in the dispersion

| Raw material | Amount (g) | % (w/w) |
|---|---|---|
| 1. Ambergum ® 1221 (2% w/w in water) | 15.00 | 0.42 |
| 2. Oligomeric composition 6 (49% w/w in water) | 4.50 | 3.10 |
| 3. Demineralised water | 30.00 | To balance |
| 4. Perfume oil | 20.00 | 28.12 |
| 5. Alcapsol ® 144 (20% w/w in water) | 0.40 | 0.11 |
| 6. Urea (50% w/w in water) | 1.00 | 0.70 |
| 7. NaOH (30% w/w in water) | 0.30 | 0.10 |
| Total | 71.20 | 100 |

Microcapsules 14:

The microcapsules were prepared as described for microcapsule 3, using oligomeric composition 6.

TABLE 14 w/w percentage of the various components introduced stepwise in the dispersion

| Raw material | Amount (g) | % (w/w) |
|---|---|---|
| 1. Ambergum ® 1221 (2% w/w in water) | 15.00 | 0.42 |
| 2. Oligomeric composition 6 (49% w/w in water) | 4.50 | 3.06 |
| 3. Demineralised water | 30.00 | To balance |
| 4. Perfume oil | 20.00 | 27.72 |
| 5. Alcapsol ® 144 (20% w/w in water) | 0.40 | 0.11 |
| 6. Urea (50% w/w in water) | 2.00 | 1.39 |
| 7. NaOH (30% w/w in water) | 0.19 | 0.08 |
| Total | 72.09 | 100 |

Microcapsules 15:

The microcapsules were prepared as described for microcapsule 2, using oligomeric composition 7.

TABLE 15 w/w percentage of the various components introduced stepwise in the dispersion

| Raw material | Amount (g) | % (w/w) |
|---|---|---|
| 1. Ambergum ® 1221 (2% w/w in water) | 15.00 | 0.42 |
| 2. Oligomeric composition 7 (41.4% w/w in water) | 4.50 | 2.61 |
| 3. Demineralised water | 30.00 | To balance |
| 4. Perfume oil | 20.00 | 28.12 |
| 5. Alcapsol ® 144 (20%) | 0.40 | 0.11 |
| 6. Urea (50% w/w in water) | 1.00 | 0.70 |
| 7. NaOH (30% w/w in water) | 0.42 | 0.18 |
| Total | 71.32 | 100 |

Microcapsules 16:

The microcapsules were prepared as described for microcapsule 3, using oligomeric composition 7.

TABLE 16 w/w percentage of the various components introduced stepwise in the dispersion

| Raw material | Amount (g) | % (w/w) |
|---|---|---|
| 1. Ambergum ® 1221 (2% w/w in water) | 15.00 | 0.42 |
| 2. Oligomeric composition 7 (41.4% w/w in water) | 4.50 | 2.58 |
| 3. Demineralised water | 30.00 | To balance |
| 4. Perfume oil | 20.00 | 27.72 |
| 5. Alcapsol ® 144 (20% w/w in water) | 0.40 | 0.11 |
| 6. Urea (50% w/w in water) | 2.00 | 1.39 |
| 7. NaOH (30% w/w in water) | 0.34 | 0.14 |
| Total | 72.24 | 100 |

Microcapsules 17:

In a 200 ml reactor, solutions of Ambergum® 1221 (15.0 g, 2 wt % in water) and oligomeric composition 6 as directly obtained in Example 1 (4.5 g) were dissolved in water (30.0 g) and stirred for 30 minutes at room temperature (pH=4.49). Perfume oil (20.0 g, Table 11) was added and the reaction mixture was sheared with ultra turrax at 24000 rpm for 2 minutes. A solution of colloidal stabilizer was introduced (Alcapsol 144, 20 wt % in water, 0.4 g, pH=4.52). The reaction mixture was heated at 40° C. for 1 h, and at 60° C. for 1 h. A solution of 1H-1,2,4-triazole-3,5-diamine (50 wt % in water, 2.0 g, >98%, Supplier: Alfa Aesar) was introduced at 60° C. and reaction mixture was stirred for 1 h. Finally, mixture was heated at 75° C. for 3 h. The resulting slurry was cooled down (pH=5.02) and neutralized with a solution of sodium hydroxide (30 wt % in water, 0.28 g, pH=7.06).

TABLE 17 w/w percentage of the various components introduced stepwise in the dispersion

| Raw material | Amount (g) | % (w/w) |
|---|---|---|
| 1. Ambergum ® 1221 (2% w/w in water) | 15.00 | 0.42 |
| 2. Oligomeric composition 6 (49% w/w in water) | 4.50 | 3.06 |
| 3. Demineralised water | 30.00 | To balance |
| 4. Perfume oil | 20.00 | 27.72 |
| 5. Alcapsol ® 144 (20% w/w in water) | 0.40 | 0.11 |
| 6. 1H-1,2,4-triazole-3,5-diamine (50% w/w in water) | 2.00 | 1.39 |
| 7. NaOH (30% w/w in water) | 0.27 | 0.08 |
| Total | 72.17 | 100 |

Microcapsules 18:

The microcapsules were prepared as described for microcapsule 3, using oligomeric composition 8.

TABLE 18 w/w percentage of the various components introduced stepwise in the dispersion

| Raw material | Amount (g) | % (w/w) |
|---|---|---|
| 1. Ambergum ® 1221 (2% w/w in water) | 15.00 | 0.42 |
| 2. Oligomers composition 8 (46.7% w/w in water) | 4.50 | 3.06 |
| 3. Demineralised water | 30.00 | 41.60 |
| 4. Perfume oil | 20.00 | 27.73 |
| 5. Alcapsol ® 144 (20% w/w in water) | 0.40 | 0.11 |
| 6. Urea (50% w/w in water) | 2.00 | 1.39 |
| 7. NaOH (30% w/w in water) | 0.22 | 0.09 |
| Total | 72.12 | 100 |

Microcapsules 19:

The microcapsules were prepared as described for microcapsule 3, using oligomeric composition 9.

TABLE 19 w/w percentage of the various components introduced stepwise in the dispersion

| Raw material | Amount (g) | % (w/w) |
|---|---|---|
| 1. Ambergum ® 1221 (2% w/w in water) | 15.00 | 0.42 |
| 2. Oligomeric composition 9 (45.8% w/w in water) | 4.50 | 2.86 |
| 3. Demineralised water | 30.00 | To balance |
| 4. Perfume oil | 20.00 | 27.73 |
| 5. Alcapsol ® 144 (20% w/w in water) | 0.40 | 0.11 |
| 6. Urea (50% w/w in water) | 2.00 | 1.39 |
| 7. NaOH (30% w/w in water) | 0.19 | 0.09 |
| Total | 72.09 | 100 |

Microcapsules 20:

In a 200 ml reactor, solutions of polyol (Ambergum® 1221, 15.0 g, 2% in water) and oligomeric composition 12 as directly obtained in Example 1 (4.5 g) were dissolved in water (30.0 g) and stirred for 30 min at room temperature (pH=5.17). Perfume oil (20.0 g, Table 11) was added and the reaction mixture was sheared with ultra turrax at 24000 rpm for 2 minutes. A solution of colloidal stabilizer was introduced (Alcapsol® 144, 20% in water, 0.4 g, pH=5.27). Reaction mixture was heated at 40° C. for 1 h, and at 60° C. for 1 h. A solution of urea (50% in water, 2.0 g) was introduced at 60° C. and reaction mixture was stirred for 1 h. Finally, mixture was heated at 75° C. for 3 h. The resulting slurry was cooled down (pH=5.31) and neutralized with a solution of sodium hydroxide (30% in water, 0.30 g, pH=7.60).

TABLE 20 w/w percentage of the various components introduced stepwise in the dispersion

| Raw material | Amount (g) | % (w/w) |
|---|---|---|
| 1. Ambergum ® 1221 (2% w/w in water) | 15.00 | 0.42 |
| 2. Oligomeric composition 12 (64% in water) | 3.40 | 3.11 |
| 3. Demineralised water | 30.00 | To balance |
| 4. Perfume oil | 20.00 | 28.13 |
| 5. Alcapsol ® 144 (20% w/w in water) | 0.40 | 0.11 |
| 6. Urea (50% w/w in water) | 2.00 | 1.41 |
| 7. NaOH (30% w/w in water) | 0.30 | 0.13 |
| Total | 70.14 | 100 |

Microcapsules 21:

The microcapsules were prepared as described for microcapsule 20 with 6.28% of oligomeric composition 12.

TABLE 21 w/w percentage of the various components introduced stepwise in the dispersion

| Raw material | Amount (g) | % (w/w) |
|---|---|---|
| 1. Ambergum ® 1221 (2% w/w in water) | 15.00 | 0.39 |
| 2. Oligomeric composition 12 (~25.9% in water) | 18.37 | 6.28 |
| 3. Demineralised water | 20.00 | To balance |
| 4. Perfume oil | 20.00 | 28.13 |
| 5. Alcapsol ® 144 (20% w/w in water) | 0.40 | 0.11 |
| 6. Urea (50% w/w in water) | 2.00 | 1.31 |
| 7. NaOH (30% w/w in water) | 0.30 | 0.10 |
| Total | 76.03 | 100 |

Microcapsules 21 was prepared with 6.28% of oligomeric composition 12 compared with microcapsules 20 prepared with 3.11% of oligomeric composition 12. Higher concentration of resin improved capsules stability. Stability of microcapsules 20 and 21 was improved compared with comparative microcapsules 5 (FIG. 6b/10).

Microcapsules 22:

The microcapsules were prepared as described for microcapsule 21 with guanazole to replace urea.

TABLE 22 w/w percentage of the various components introduced stepwise in the dispersion

| Raw material | Amount (g) | % (w/w) |
|---|---|---|
| 1. Ambergum ® 1221 (2% w/w in water) | 15.00 | 0.39 |
| 2. Oligomeric composition 12 (~25.9% in water) | 18.67 | 6.27 |
| 3. Demineralised water | 20.00 | To balance |
| 4. Perfume oil | 20.00 | 28.13 |
| 5. Alcapsol ® 144 (20% w/w in water) | 0.40 | 0.11 |
| 6. Guanazole (50% w/w in water) | 2.00 | 1.31 |
| 7. NaOH (30% w/w in water) | 0.35 | 0.10 |
| Total | 76.42 | 100 |

Microcapsules 21 were coated with urea compared with microcapsules 22 coated with guanazole. Guanazole increased capsules stability. Stability of microcapsules 21 and 22 was improved compared with comparative microcapsules 5 (FIG. 7a/10).

Microcapsules 23:

In a 200 ml reactor, solutions of polyol (Ambergum® 1221, 30.0 g, 2% in water) with 1H-1,2,4-triazole-3,5-diamine (2 g) and oligomeric composition 12 as directly obtained in Example 1 (18.85 g, 25% in water) were stirred (pH=5.42). Perfume oil (20.0 g) was added and the reaction mixture was sheared with ultra turrax at 24000 rpm for 2 min. The mixture was heated at 60° C. for 6 h. The resulting slurry was cooled down (pH=4.94) and neutralized with a solution of sodium hydroxide (30% in water, 0.42 g, pH=6.53).

TABLE 23 w/w percentage of the various components introduced stepwise in the dispersion

| Raw material | Amount (g) | % (w/w) |
|---|---|---|
| 1. Ambergum ® 1221 (2% w/w in water) | 30.00 | 0.84 |
| 2. Oligomeric composition 12 (~25.2% in water) | 18.85 | 6.67 |
| 3. Guanazole (50% w/w in water) | 2.00 | 2.49 |
| 4. Perfume oil | 20.00 | 28.05 |
| 5. NaOH (30% w/w in water) | 0.42 | 0.21 |
| Total | 71.27 | 100 |

Microcapsules 24:

The microcapsules were prepared as described for microcapsule 23 at 70° C.

TABLE 24 w/w percentage of the various components introduced stepwise in the dispersion

| Raw material | Amount (g) | % (w/w) |
|---|---|---|
| 1. Ambergum ® 1221 (2% w/w in water) | 30.00 | 0.84 |
| 2. Oligomeric composition 12 (~25.2% in water) | 18.85 | 6.67 |
| 3. Guanazole (50% w/w in water) | 2.00 | 2.49 |
| 4. Perfume oil | 20.00 | 28.05 |
| 5. NaOH (30% w/w in water) | 0.42 | 0.21 |
| Total | 71.27 | 100 |

Microcapsules 25:

The microcapsules were prepared as described for microcapsule 23 at 80° C.

TABLE 25 w/w percentage of the various components introducedstepwise in the dispersion

| Raw material | Amount (g) | % (w/w) |
|---|---|---|
| 1. Ambergum ® 1221 (2% w/w in water) | 30.00 | 0.84 |
| 2. Oligomeric composition 12 (~25.2% in water) | 18.85 | 6.67 |
| 3. Guanazole (50% w/w in water) | 2.00 | 2.49 |
| 4. Perfume oil | 20.00 | 28.05 |
| 5. NaOH (30% w/w in water) | 0.42 | 0.21 |
| Total | 71.27 | 100 |

Microcapsules 23 were prepared at 60° C. for 6 h, whereas microcapsules 24 and 25 were prepared at 70° C. and 80° C., respectively, for 6 h. Higher temperature of polymerization gave more stable microcapsules. Stability of microcapsules 23, 24 and 25 was improved compared with comparative microcapsules 5 (FIG. 7b/10).

Microcapsules 26:

The microcapsules were prepared as described for microcapsule 23 with 1.88% w/w of guanazole.

TABLE 26 w/w percentage of the various components introduced stepwise in the dispersion

| Raw material | Amount (g) | % (w/w) |
|---|---|---|
| 1. Ambergum ® 1221 (2% w/w in water) | 30.00 | 0.84 |
| 2. Oligomeric composition 12 (~25.2% in water) | 18.85 | 6.67 |
| 3. Guanazole (50% w/w in water) | 1.50 | 1.88 |
| 4. Perfume oil | 20.00 | 28.24 |
| 5. NaOH (30% w/w in water) | 0.44 | 0.19 |
| Total | 70.81 | 100 |

Microcapsules 27:

The microcapsules were prepared as described for microcapsule 23 with 1.26% w/w of guanazole.

TABLE 27 w/w percentage of the various components introduced stepwise in the dispersion

| Raw material | Amount (g) | % (w/w) |
|---|---|---|
| 1. Ambergum ® 1221 (2% w/w in water) | 30.00 | 0.85 |
| 2. Oligomeric composition 12 (~25.2% in water) | 18.85 | 6.67 |
| 3. Guanazole (50% w/w in water) | 1.00 | 1.26 |
| 4. Perfume oil | 20.00 | 28.24 |
| 5. NaOH (30% w/w in water) | 0.38 | 0.16 |
| Total | 70.21 | 100 |

Microcapsules 28:

The microcapsules were prepared as described for microcapsule 23 with 1.63% w/w of to guanazole.

TABLE 28 w/w percentage of the various components introduced stepwise in the dispersion

| Raw material | Amount (g) | % (w/w) |
|---|---|---|
| 1. Ambergum ® 1221 (2% w/w in water) | 30.00 | 0.85 |
| 2. Oligomeric composition 12 (~25.2% in water) | 18.85 | 6.67 |
| 3. Guanazole (50% w/w in water) | 1.30 | 1.63 |
| 4. Perfume oil | 20.00 | 28.39 |
| 5. NaOH (30% w/w in water) | 0.35 | 0.15 |
| Total | 70.45 | 100 |

Microcapsules 29:

The microcapsules were prepared as described for microcapsule 23 with 1.76% w/w of guanazole.

TABLE 29 w/w percentage of the various components introduced stepwise in the dispersion

| Raw material | Amount (g) | % (w/w) |
|---|---|---|
| 1. Ambergum ® 1221 (2% w/w in water) | 30.00 | 0.85 |
| 2. Oligomeric composition 12 (~25.2% in water) | 18.85 | 6.67 |
| 3. Guanazole (50% w/w in water) | 1.40 | 1.76 |
| 4. Perfume oil | 20.00 | 28.31 |
| 5. NaOH (30% w/w in water) | 0.40 | 0.17 |
| Total | 70.65 | 100 |

Microcapsules 23 were coated with 2.49% of guanazole compared with microcapsules 26, 27, 28 and 29, coated with 1.88%, 1.26%, 1.63% and 1.76% of guanazole, respectively. Concentration above 1.76% is optimal. Stability of microcapsules 23, 26, 27, 28 and 29 was improved compared with comparative microcapsules 5 (FIG. 8a/10).

Microcapsules 30:

The microcapsules were prepared as described for microcapsule 29, using oligomeric composition 10.

TABLE 30 w/w percentage of the various components introduced stepwise in the dispersion

| Raw material | Amount (g) | % (w/w) |
|---|---|---|
| 1. Ambergum ® 1221 (2% w/w in water) | 30.00 | 0.86 |
| 2. Oligomeric composition 10 (~23.5% in water) | 18.31 | 6.15 |
| 3. Guanazole (50% w/w in water) | 1.40 | 1.77 |
| 4. Perfume oil | 20.00 | 28.55 |
| 5. NaOH (30% w/w in water) | 0.35 | 0.15 |
| Total | 70.06 | 100 |

Microcapsules 31:

The microcapsules were prepared as described for microcapsule 29, using oligomeric composition 11.

TABLE 31 w/w percentage of the various components introduced stepwise in the dispersion

| Raw material | Amount (g) | % (w/w) |
|---|---|---|
| 1. Ambergum ® 1221 (2% w/w in water) | 30.00 | 0.87 |
| 2. Oligomeric composition 11 (~25% in water | 17.26 | 6.24 |
| 3. Guanazole (50% w/w in water) | 1.40 | 1.80 |
| 4. Perfume oil | 20.00 | 28.94 |
| 5. NaOH (30% w/w in water) | 0.45 | 0.20 |
| Total | 69.11 | 100 |

Microcapsules 32:

The microcapsules were prepared as described for microcapsule 29, using oligomeric composition 6.

TABLE 32 w/w percentage of the various components introduced stepwise in the dispersion

| Raw material | Amount (g) | % (w/w) |
|---|---|---|
| 1. Ambergum ® 1221 (2% w/w in water) | 40.46 | 0.83 |
| 2. Oligomeric composition 6 (~27.2% in water) | 27.24 | 7.63 |
| 3. Guanazole (50% w/w in water) | 1.89 | 1.75 |
| 4. Perfume oil | 27.00 | 27.82 |
| 5. NaOH (30% w/w in water) | 0.47 | 0.15 |
| Total | 97.06 | 100 |

Microcapsules 29 were prepared with oligomeric composition 12, having a melamine/urea molar ratio of 1/2.45 compared with microcapsules 30 (1/1.6), 31 (1/2), and 32 (1/3). Molar ratio below 4.5 gave more stable microcapsules. Stability of microcapsules 29, 30, 31 and 32 was improved compared with comparative microcapsules 5 (FIG. 8b/10).

Microcapsules 33:

In a 200 ml reactor, a solution of colloidal stabilizer (Alcapsol® 144, 20% in water, 3.5 g, pH=5.75) in water (6.50 g) was dissolved in oligomeric composition 13 as directly obtained in Example 1 (40.29 g). Perfume oil (21.00 g) was added and the reaction mixture was sheared with ultra turrax at 20000 rpm for 2 minutes. pH was adjusted at 5.43 with formic acid (0.18 g). Reaction mixture was stirred at 300 r.p.m. and heated at 45° C. for 1.5 h then at 60° C. for 1.5 h, and finally at 75° C. for 2 h. The resulting slurry was cooled down (pH=5.40) and neutralized with a solution of sodium hydroxide (0.43 g, pH=7.16).

TABLE 33 w/w percentage of the various components
introduced stepwise in the dispersion

| Raw material | Amount (g) | % (w/w) |
|---|---|---|
| 1. Alcapsol ® 144 (20% w/w in water) | 3.50 | 0.97 |
| 2. Demineralised water | 6.50 | To balance |
| 3. Oligomeric composition 13 (10.66% in water) | 40.29 | 5.97 |
| 4. Perfume oil | 21.00 | 29.21 |
| 5. Formic acid | 0.18 | 0.25 |
| 6. NaOH (30% w/w in water) | 0.43 | 0.18 |
| Total | 71.90 | 100 |

Microcapsules 34:

In a 200 ml reactor, a solution of colloidal stabilizer (Alcapsol® 144, 3.50 g, pH=5.75) in water (6.50 g) was dissolved in oligomeric composition 13 as directly obtained in Example 1 (40.29 g). Perfume oil (21.00 g) was added and the reaction mixture was sheared with ultra turrax at 20000 rpm for 2 minutes. pH was adjusted at 5.42 with formic acid (0.20 g). Reaction mixture was stirred at 300 r.p.m. and heated at 45° C. for 1 h then at 60° C. for 1 h, and finally at 80° C. for 3 h. The resulting slurry was cooled down (pH=5.45) and neutralized with a solution of sodium hydroxide (0.23 g, pH=6.82).

TABLE 34 w/w percentage of the various components
introduced stepwise in the dispersion

| Raw material | Amount (g) | % (w/w) |
|---|---|---|
| 1. Alcapsol ® 144 (20% w/w in water) | 3.50 | 0.99 |
| 2. Demineralised water | 6.50 | To balance |
| 3. Oligomeric composition 13 (10.66% in water) | 40.29 | 6.07 |
| 4. Perfume oil | 21.00 | 29.70 |
| 5. Formic acid | 0.20 | 0.28 |
| 6. NaOH (30% w/w in water) | 0.23 | 0.10 |
| Total | 70.70 | 100 |

Microcapsules 35:

In a 200 ml reactor, a solution of colloidal stabilizer (Alcapsol® 144, 3.5 g, pH=5.75) in water (6.50 g) was dissolved in oligomeric composition 13 as directly obtained in Example 1 (40.29 g). Perfume oil (21.0 g) was added and the reaction mixture was sheared with ultra turrax at 20000 rpm for 2 minutes. pH was adjusted at 5.42 with formic acid (0.17 g). Reaction mixture was stirred at 300 r.p.m. and heated at 55° C. for 3 h then at 75° C. for 2 h. The resulting slurry was cooled down (pH=5.58) and neutralized with a solution of sodium hydroxide (30% in water, 0.61 g, pH=6.94).

TABLE 35 w/w percentage of the various components
introduced stepwise in the dispersion

| Raw material | Amount (g) | % (w/w) |
|---|---|---|
| 1. Alcapsol ® 144 (20% w/w in water) | 3.50 | 0.97 |
| 2. Demineralised water | 6.50 | To balance |
| 3. Oligomeric composition 13 (10.66% in water) | 40.29 | 5.96 |
| 4. Perfume oil | 21.00 | 29.13 |
| 5. Formic acid | 0.17 | 0.24 |
| 6. NaOH (30% w/w in water) | 0.61 | 0.25 |
| Total | 72.10 | 100 |

Microcapsules 33 were prepared with oligomeric composition 13 at 45° C. for 1.5 h, 60° C. for 1.5 h and finally at 75° C. for 2 h, compared with microcapsules 34, prepared at 45° C. for 1 h, 60° C. for 1 h and 80° C. for 3 h, and with microcapsules 35, prepared at 55° C. for 3 h and 75° C. for 2 h. Stability of microcapsules 33, 34 and 35 was improved compared with comparative microcapsules 5 (FIG. 9a/10).

Microcapsules 36:

In a 200 ml reactor, oligomeric composition 13, as directly obtained in Example 1 (40.29 g), was diluted with water (10.00 g) and perfume oil (21.00 g) was added. Reaction mixture was sheared with ultra turrax at 20000 rpm for 2 minutes. pH was adjusted at 5.40 with formic acid (0.24 g). Reaction mixture was stirred at 300 r.p.m. and heated at 45° C. for 1 h then at 60° C. for 1 h, and finally at 75° C. for 3 h. The resulting slurry was cooled down (pH=5.50) and neutralized with a solution of sodium hydroxide (30% in water, 0.2 g, pH=6.67).

TABLE 36 w/w percentage of the various components
introduced stepwise in the dispersion

| Raw material | Amount (g) | % (w/w) |
|---|---|---|
| 1. Oligomeric composition 13 (10.66% in water) | 40.29 | 5.99 |
| 2. Demineralised water | 10.00 | To balance |
| 3. Perfume oil | 21.00 | 29.28 |
| 4. Formic acid | 0.24 | 0.33 |
| 5. NaOH (30% w/w in water) | 0.20 | 0.12 |
| Total | 71.73 | 100 |

Microcapsules 37:

In a 200 ml reactor, a solution of colloidal stabilizer (Alcapsol® 144, 7.00 g, pH=5.75) in water (3.00 g) was dissolved in oligomeric composition 13 as directly obtained in Example 1 (40.29 g). Perfume oil (21.00 g) was added and the reaction mixture was sheared with ultra turrax at 20000 rpm for 2 minutes. pH was adjusted at 5.40 with formic acid (0.25 g). Reaction mixture was stirred at 300 r.p.m. and heated at 45° C. for 1 h then at 60° C. for 1 h, and finally at 75° C. for 3 h. The resulting slurry was cooled down (pH=5.50) and neutralized with a solution of sodium hydroxide (30% in water, 0.31 g, pH=6.70).

TABLE 37 w/w percentage of the various components
introduced stepwise in the dispersion

| Raw material | Amount (g) | % (w/w) |
|---|---|---|
| 1. Alcapsol ® 144 (20% w/w in water) | 7.00 | 1.95 |
| 2. Demineralised water | 3.00 | To balance |
| 3. Oligomeric composition 13 (10.66% in water) | 40.29 | 5.98 |
| 4. Perfume oil | 21.00 | 29.23 |

TABLE 37-continued w/w percentage of the various components introduced stepwise in the dispersion

| Raw material | Amount (g) | % (w/w) |
|---|---|---|
| 5. Formic acid | 0.25 | 0.24 |
| 6. NaOH (30% w/w in water) | 0.31 | 0.25 |
| Total | 71.85 | 100 |

Microcapsules 36 were prepared with oligomeric composition 13 in the absence of polyol and colloidal stabilizer whereas microcapsules 34 and 37 contain 1% and 2% of colloidal stabilizer, respectively. Stability of microcapsules 34, 36 and 37 was improved compared with comparative microcapsules 5 (FIG. 9b/10).

Microcapsules 38:

In a 200 ml reactor, oligomeric composition 13 as directly obtained in Example 1 (40.29 g) was diluted with water (10.00 g). Perfume oil (21.00 g) was added. Reaction mixture was sheared with ultra turrax at 20000 rpm for 2 minutes. pH was adjusted at 5.42 with formic acid (0.23 g). Reaction mixture was stirred at 300 r.p.m. and heated at 45° C. for 1 h30 then at 60° C. for 1 h30, and finally at 75° C. for 2 h. The resulting slurry was cooled down (pH=5.54) and neutralized with a solution of sodium hydroxide (30% in water, 0.23 g, pH=6.92).

TABLE 38 w/w percentage of the various components introduced stepwise in the dispersion

| Raw material | Amount (g) | % (w/w) |
|---|---|---|
| 1. Oligomeric composition 13 (10.66% in water) | 40.29 | 6.07 |
| 2. Demineralised water | 10.00 | To balance |
| 3. Perfume oil | 21.00 | 29.68 |
| 4. Formic acid | 0.23 | 0.33 |
| 5. NaOH (30% w/w in water) | 0.23 | 0.10 |
| Total | 70.75 | 100 |

Microcapsules 39:

In a 200 ml reactor, polyol (Ambergum® 1221, 0.69 g) was dissolved in water (10.00 g) and was added into oligomeric composition 13 as directly obtained in Example 1 (40.29 g). Perfume oil (21.00 g) was added and the reaction mixture was sheared with ultra turrax at 21000 rpm for 2 minutes. pH was adjusted at 5.39 with formic acid (0.17 g). Reaction mixture was stirred at 300 r.p.m. and heated at 45° C. for 1 h then at 60° C. for 1 h, and finally at 75° C. for 3 h. The resulting slurry was cooled down (pH=5.39) and neutralized with a solution of sodium hydroxide (30% in water, 0.18 g, pH=6.68).

TABLE 39 w/w percentage of the various components introduced stepwise in the dispersion

| Raw material | Amount (g) | % (w/w) |
|---|---|---|
| 1. Ambergum ® 1221 (2% w/w in water) | 0.69 | 0.95 |
| 2. Demineralised water | 10.00 | To balance |
| 3. Oligomeric composition 13 (10.66% in water) | 40.29 | 5.94 |
| 4. Perfume oil | 21.00 | 29.03 |

TABLE 39-continued w/w percentage of the various components introduced stepwise in the dispersion

| Raw material | Amount (g) | % (w/w) |
|---|---|---|
| 5. Formic acid | 0.17 | 0.24 |
| 6. NaOH (30% w/w in water) | 0.18 | 0.07 |
| Total | 72.33 | 100 |

Microcapsules 40:

The microcapsules were prepared as described for microcapsule 39, using oligomeric composition 13 and sucralose to replace Ambergum® 1221 as polyol.

TABLE 40 w/w percentage of the various components introduced stepwise in the dispersion

| Raw material | Amount (g) | % (w/w) |
|---|---|---|
| 1. Sucralose | 0.70 | 0.97 |
| 2. Demineralised water | 10.00 | To balance |
| 3. Oligomeric composition 14 (10.66% in water) | 40.29 | 5.93 |
| 4. Perfume oil | 21.00 | 28.99 |
| 5. Formic acid | 0.20 | 0.28 |
| 6. NaOH (30% w/w in water) | 0.25 | 0.10 |
| Total | 72.44 | 100 |

Microcapsules 36 were prepared with oligomeric composition 13 in the absence of polyol. Microcapsules 39 and 40 contain 1% of two different polyols. The presence of polyol in the present invention's process and product is not mandatory to improve performance. Stability of microcapsules 36, 39 and 40 was improved compared with comparative microcapsules 5 (FIG. 10a/10)

Microcapsules 41:

The microcapsules were prepared as described for microcapsule 36, using oligomeric composition 14.

TABLE 41 w/w percentage of the various components introduced stepwise in the dispersion

| Raw material | Amount (g) | % (w/w) |
|---|---|---|
| 1. Oligomeric composition 14 (8.54% in water) | 50.78 | 7.01 |
| 2. Demineralised water | 10.00 | To balance |
| 3. Perfume oil | 21.00 | 29.08 |
| 4. Formic acid | 0.21 | 0.29 |
| 5. NaOH (30% w/w in water) | 0.23 | 0.10 |
| Total | 71.73 | 100 |

Microcapsules 36 and 41 were prepared with oligomeric composition 13 and 14, respectively. Both microcapsules are stable. Stability of microcapsules 36 and 41 was improved compared with comparative microcapsules 5 (FIG. 10b/10).

Example 4

Preparation of Comparative Microcapsules, Out of the Scope of the Present Invention Attempt to obtain core-shell microcapsules with the following conditions provided the results reported in the Table herein below:

TABLE 1 attempts to form microcapsules with comparative oligomeric compositions

| Attempt | Experimental condition | Comparative oligomers | Results |
|---|---|---|---|
| 1 | as described for microcapsule 1 | Comparative oligomer 1 | No stable dispersion was obtained - no microcapsules were obtained |
| 2 | as described for microcapsule 3 | Comparative oligomer 1 | No stable dispersion was obtained - no microcapsules were obtained |
| 3 | as described for microcapsule 1 | Comparative oligomer 2 | No stable dispersion was obtained - no microcapsules were obtained |
| 4 | as described for microcapsule 2 | Comparative oligomer 2 | No stable dispersion was obtained - no microcapsules were obtained |
| 5 | as described for microcapsule 3 | Comparative oligomer 2 | No stable dispersion was obtained - no microcapsules were obtained |
| 6 | as described for microcapsule 1 | Comparative oligomer 4 | No stable dispersion was obtained - no microcapsules were obtained |
| 7 | as described for microcapsule 3 | Comparative oligomer 4 | No stable dispersion was obtained - no microcapsules were obtained |

Comparative Microcapsules 1: (Microcapsules Obtained Using Prior Art Oligomeric Composition)

The microcapsules were prepared as described for microcapsule 1, using comparative oligomers 3 (according to prior art WO 2009/100553).

TABLE 2 w/w percentage of the various components introduced stepwise in the dispersion

| Raw material | Amount (g) | % (w/w) |
|---|---|---|
| 1. Ambergum ® 1221 (2% w/w in water) | 15.00 | 0.43 |
| 2. Comparative oligomers 3 (64% w/w in water) | 4.50 | 4.11 |
| 3. Demineralised water | 30.00 | To balance |
| 4. Perfume oil | 20.00 | 28.42 |
| 5. Alcapsol ® 144 (20% w/w in water) | 0.40 | 0.11 |
| 6. NaOH (30% w/w in water) | 0.22 | 0.20 |
| Total | 70.12 | 100 |

From FIGS. 1a to 5a it is evident that the present invention's core-shell microcapsules, obtained from the respective oligomeric composition according to the invention, perform all better than the microcapsules obtained according to the prior art. The prior art capsules do not show a thermal stability (no plateau in the TGA) indicating a leakage of the oil throughout the shell, while all the invention's microcapsules show a significantly improved thermal stability (a plateau in the TGA) indicating no leakage of the oil throughout the shell (independently from the nature of the polyamine component and/or of the fact that step 2) of the invention's process is performed or not, e.g. microcapsules 1 and 12, or of the nature of the diamino compound e.g. microcapsules 17).

Comparative Microcapsules 2: (Microcapsules Obtained Using Prior Art Oligomeric Composition and the Present Invention's Process)

The microcapsules were prepared as described for microcapsule 2, using comparative oligomers 3 (according to prior art WO 2009/100553).

TABLE 3 w/w percentage of the various components introduced stepwise in the dispersion

| Raw material | Amount (g) | % (w/w) |
|---|---|---|
| 1. Ambergum ® 1221 (2% w/w in water) | 15.00 | 0.42 |
| 2. Comparative oligomers 3 (64% w/w in water) | 4.50 | 4.04 |
| 3. Demineralised water | 30.00 | To balance |
| 4. Perfume oil | 20.00 | 28.12 |
| 5. Alcapsol ® 144 (20% w/w in water) | 0.40 | 0.11 |
| 6. Urea (50% w/w in water) | 1.00 | 0.70 |
| 7. NaOH (30% w/w in water) | 0.31 | 0.18 |
| Total | 71.21 | 100 |

Comparative Microcapsules 3: (Microcapsules Obtained Using Prior Art Oligomeric Composition and the Present Invention's Process)

The microcapsules were prepared as described for microcapsule 3, using comparative oligomers 3 (according to prior art WO 2009/100553).

TABLE 4 w/w percentage of the various components introduced stepwise in the dispersion

| Raw material | Amount (g) | % (w/w) |
|---|---|---|
| 1. Ambergum ® 1221 (2% w/w in water) | 15.00 | 0.42 |
| 2. Comparative oligomers 3 (64% w/w in water) | 4.50 | 3.99 |
| 3. Demineralised water | 30.00 | To balance |
| 4. Perfume oil | 20.00 | 27.72 |
| 5. Alcapsol ® 144 (20% w/w in water) | 0.40 | 0.11 |
| 6. Urea (50% w/w in water) | 2.00 | 1.39 |
| 7. NaOH (30% w/w in water) | 0.28 | 0.14 |
| Total | 72.18 | 100 |

From FIG. 6a it is evident that the invention's process is specifically designed for the invention's oligomeric composition (microcapsules 9). Indeed, when the invention's process is applied to the prior art teaching, the microcapsules thus obtained (comparative microcapsules 2 and 3) performed significantly worse than the prior art microcapsules (comparative microcapsule 1).

Comparative Microcapsules 4: (Microcapsules Obtained Using Prior Art Oligomeric Composition and the Present Invention's Process)

The microcapsules were prepared as described for microcapsule 3, using comparative oligomers 5.

TABLE 5 w/w percentage of the various components introduced stepwise in the dispersion

| Raw material | Amount (g) | % (w/w) |
|---|---|---|
| 1. Ambergum ® 1221 (2% w/w in water) | 15.00 | 0.42 |
| 2. Comparative oligomers 5 (47.9 % w/w in water) | 4.50 | 3.99 |
| 3. Demineralised water | 30.00 | To balance |
| 4. Perfume oil | 20.00 | 27.72 |
| 5. Alcapsol ® 144 (20% w/w in water) | 0.40 | 0.11 |
| 6. Urea (50% w/w in water) | 2.00 | 1.39 |
| 7. NaOH (30% w/w in water) | 0.28 | 0.14 |
| Total | 72.18 | 100 |

From FIG. 5b it is evident that working with an oligomeric composition having a molar excess of $C_{4-6}$ 2,2-dialkoxyethanal compared to the glyoxal (comparative microcapsule 4), provides microcapsules which are not stable; while working with the invention's oligomeric composition provides microcapsules which are stable.

Comparative Microcapsules 5: (Microcapsules Obtained Using Prior Art Oligomeric Composition and Invention's Process)

The microcapsules were prepared as described for microcapsule 40, using comparative oligomers 3 (according to prior art WO 2009/100553).

TABLE 6 w/w percentage of the various components introduced stepwise in the dispersion

| Raw material | Amount (g) | % (w/w) |
|---|---|---|
| 1. Colloidal stabilizer (Gantrez AN-119BF) | 0.81 | 1.49 |
| 2. Demineralised water | 25.00 | To balance |
| 3. Polyol (Resorcinol, 30% in water) | 2.00 | 1.10 |
| 4. Comparative oligomers 3 (~53.9% in water) | 5.51 | 4.19 |
| 5. Perfume oil | 20.00 | 36.79 |
| 6. NaOH (30% in water) | 0.35 | 0.55 |
| Total | 53.67 | 100 |

Comparative Microcapsules 6: (Microcapsules Obtained Using Prior Art Oligomeric Composition and the Present Invention's Process)

The microcapsules were prepared as described for microcapsule 27, using comparative oligomers 3 (according to prior art WO 2009/100553).

TABLE 7 w/w percentage of the various components introduced stepwise in the dispersion

| Raw material | Amount (g) | % (w/w) |
|---|---|---|
| 1. Ambergum ® 1221 (2% w/w in water) | 30.00 | 0.84 |
| 2. Comparative oligomers 3 (~53.9% in water) | 5.53 | 5.14 |
| 3. Guanazole | 2.00 | 2.49 |
| 4. Perfume oil | 20.00 | 28.05 |
| 5. NaOH (30% in water) | 0.42 | 0.21 |
| Total | 57.95 | 100 |

Example 5

Use in Application of the Invention Microcapsules

Body Wash Application

TABLE 1A

| Body wash formulation | |
|---|---|
| Ingredients | % w/w |
| 1. Water deionised | 58.40 |
| 2. Carbopol Aqua CC Polymer Polyacrylate-1 Crosspolymer (Noveon) | 8.00 |
| 3. Citric Acid (40% aq. sln) Citric Acid (Merck) | 0.50 |
| 4. Zetesol AO 328 U Sodium C12-C15 Pareth Sulfate (ZSCHIMMER & SCHWARZ) | 25.00 |
| 5. Tego Betain F 50 Cocamidopropyl Betaine (GOLDSCHMIDT AG (STEINAU)) | 4.00 |

TABLE 1A-continued

| Body wash formulation | |
|---|---|
| Ingredients | % w/w |
| 6. Glydant Plus Liquid DMDM Hydantoin (and) Iodopropynyl Butylcarbamate (LONZA) | 0.10 |
| 7. Sodium Chloride (20% aq. sln) | 4.00 |

Capsules were introduced in body wash formulation, described in Table 1A to obtain a concentration of perfume at 0.2% w/w. Dispersions were stored at room temperature for 24 hours. The body wash formulation (1 ml) was diluted in water (4 ml) and then extracted with isooctane containing 1,4-dibromobenzene as internal standard (5 ml). Organic solutions are then analyzed by GC to measure the leakage of perfume. The results on oil-leakage of the microcapsules are reported in Table 1B.

TABLE 1B

| Leakage in body wash application | |
|---|---|
| Microcapsules | Oil leakage* (% w/w) |
| Microcapsules 22 | 18 |
| Microcapsules 24 | 9 |
| Microcapsules 25 | 3 |
| Microcapsules 29 | 6 |
| Microcapsules 30 | 9 |
| Microcapsules 33 | 10 |
| Microcapsules 34 | 5 |
| Microcapsules 35 | 9 |
| Microcapsules 36 | 3 |
| Microcapsules 38 | 6 |
| Microcapsules 39 | 4 |
| Microcapsules 40 | 3 |
| Microcapsules 41 | 4 |
| Comparative microcapsule 5 | 42 |
| Comparative microcapsule 6 | 58 |

*after 24 hours in the pure base at room temperature

As can be seen from Table 1B, all invention's microcapsules are more stable toward oil-leakage upon storage when compared to prior art microcapsules which are $CH_2O$-free.

Liquid Detergent Application

Capsules were introduced in liquid detergent (composition in Table 2A), with a concentration of perfume at 0.2% w/w. Dispersions were stored at room temperature for 24 hours An aliquot of liquid detergent (1 ml) was diluted in water (4 ml) and then extracted with isooctane (5 ml) containing 1,4-dibromobenzene as internal standard (150 mg/l). Organic solutions were then analyzed by GC to measure the leakage of perfume. The results on oil-leakage of the microcapsules are reported in Table 2B.

TABLE 2A

| Liquid detergent formulation | |
|---|---|
| Ingredients | % w/w |
| 1. Borax | 1-2 |
| 2. Citric Acid | 2-3 |
| 3. Diethylenetriamine Pentaacetate (Sodium Salt) | 0.1-0.5 |
| 4. Amylase | 0.1-0.2 |
| 5. Protease | 0.1-0.2 |
| 6. Disodium Diaminostilbene Disulfonate | 0.0001-0.001 |
| 7. Diquaternium Ethoxy Sulfate | 0.1-0.2 |
| 8. Polyethyleneimine Ethoxylate | 0.1-1 |
| 9. Calcium Formate | 0.01-5 |

TABLE 2A-continued

Liquid detergent formulation

| Ingredients | % w/w |
|---|---|
| 10. Dimethicone | 0.001-0.005 |
| 11. Ethanolamine | 0.5-5 |
| 12. Propylene Glycol | 0.05-0.1 |
| 13. Sodium Formate | 0.01-5 |
| 14. Alcoholethoxy Sulfate | 7-8 |
| 15. Lauramine Oxide | 1-6 |
| 16. Laureth-9 | 1-5 |
| 17. Linear Alkylbenzene Sulfonate | 1-2 |
| 18. Water | up to 95 |

TABLE 2B

Leakage in liquid detergent application

| Microcapsules | Oil leakage* (% w/w) |
|---|---|
| Microcapsules 24 | 9 |
| Microcapsules 25 | 8 |
| Microcapsules 29 | 9 |
| Microcapsules 30 | 8 |
| Microcapsules 33 | 17 |
| Microcapsules 34 | 11 |
| Microcapsules 35 | 9 |
| Microcapsules 36 | 6 |
| Microcapsules 37 | 27 |
| Microcapsules 38 | 22 |
| Microcapsules 39 | 7 |
| Microcapsules 40 | 6 |
| Microcapsules 41 | 5 |
| Comparative microcapsule 5 | 94 |
| Comparative microcapsule 6 | 66 |

*after 24 hours in the pure base at room temperature

As can be seen from Table 2B all invention microcapsules are more stable toward oil-leakage upon storage when compared to prior art microcapsules which are $CH_2O$-free.

Softener Application

Microcapsules were diluted in a fabric softener (composition: Stepantex® VK90 (Stepan) 16.5%, calcium chloride 0.2%, water 83.3%) to obtain a concentration of perfume at 0.8% w/w. Dispersions were stored at room temperature for 24 hours. An aliquot of softener (1 ml) was diluted in water (4 ml) and then extracted with isooctane (5 ml) containing 1,4-dibromobenzene as internal standard (150 mg/L). Organic solutions were then analyzed by GC to measure the leakage of perfume. The results on oil-leakage of the microcapsules are reported in Table 3B.

TABLE 3B

Leakage in fabric softener application

| Microcapsules | Oil leakage* (% w/w) |
|---|---|
| Microcapsules 25 | 17 |
| Microcapsules 33 | 13 |
| Microcapsules 34 | 9 |
| Microcapsules 35 | 7 |
| Microcapsules 36 | 4 |
| Microcapsules 38 | 5 |
| Microcapsules 39 | 4 |
| Microcapsules 40 | 2 |
| Microcapsules 41 | 5 |
| Comparative microcapsule 5 | 92 |
| Comparative microcapsule 6 | 73 |

*after 24 hours in the pure base at room temperature

As can be seen from Table 3B all invention microcapsules are more stable toward oil-leakage upon storage when compared to prior art microcapsules which are $CH_2O$-free.

What is claimed is:

1. A formaldehyde-free core-shell microcapsule having a mean diameter between about 1 and 600 μm and comprising an external solid oligomer-based shell or wall and an internal continuous oil phase enclosed by the external shell, with the oligomer based shell comprising the reaction product of:
   1) a polyamine component in the form of melamine or of a mixture of melamine and at least one $C_{1-4}$ compound comprising two $NH_2$ functional groups;
   2) an aldehyde component in the form of a mixture of glyoxal, a $C_{4-6}$ 2,2-dialkoxy-ethanal, said mixture having a molar ratio glyoxal/$C_{4-6}$ 2,2-dialkoxy-ethanal comprised between about 1/1 and 10/1; and
   3) a protic acid catalyst.

2. The core-shell microcapsule of claim 1, having a mean diameter between about 5 and 200 μm.

3. The core-shell microcapsule of claim 1, wherein the polyamine component of the oligomeric composition is a mixture of melamine and at least one $C_{1-4}$ compound comprising two $NH_2$ functional groups and said $C_{1-4}$ compound comprising two $NH_2$ functional groups is urea, 1H-1,2,4-triazole-3,5-diamine or a mixture thereof.

4. The core-shell microcapsule of claim 3, wherein said mixture of melamine and $C_{1-4}$ compound has a melamine/$C_{1-4}$ compound ratio of between about 2/1 and 1/3.

5. The core-shell microcapsule of claim 1, wherein said aldehyde component has a molar ratio of glyoxal/2,2-dialkoxy-ethanal that is between about 2.2/1 and 6.5/1.

6. The core-shell microcapsule of claim 1, wherein said $C_{4-6}$ dialkoxyethanal is 2,2-dimethoxy-ethanal, 2,2-diethoxy-ethanal or mixtures thereof.

7. The core-shell microcapsule of claim 1, wherein said aldehyde component further comprises a glyoxalate.

8. The core-shell microcapsule of claim 7, wherein said glyoxalate has a molar ratio glyoxal/glyoxalate of between about 4/1 and 1/1.

9. The core-shell microcapsule of claim 1, wherein the polyamine component and the aldehyde component are admixed in a ratio such that the (total amine functional group)/(total free aldehyde functional group) has a molar ratio between about 2/1 and 1/2.

10. The core-shell microcapsule of claim 1, wherein said protic acid catalyst is selected amongst mineral acids, $C_{1-6}$ mono or dicarboxylic acids and mixtures thereof.

11. The core-shell microcapsule of claim 1, which is obtainable by a process which comprises the steps of:
    1) preparing an oil-in-water dispersion, wherein the droplet size is between 1 and 600 μm, and comprising the oligomeric composition;
    2) optionally adding to the dispersion a further $C_{1-4}$ compound comprising two $NH_2$ functional groups;
    3) heating said dispersion; and
    4) cooling said dispersion, optionally with drying, to obtain the core-shell microcapsule.

12. The core-shell microcapsule of claim 11, wherein said oil is a perfume oil, and the dispersion comprises between about 10% and 50% of oil, percentage being expressed on a w/w basis relative to the total weight of the dispersion.

13. The core-shell microcapsule of claim 11, wherein said dispersion comprises between about 1% and 10% of oligomeric composition, percentage being expressed on a w/w basis relative to the total weight of the dispersion.

14. The core-shell microcapsule of claim 11, wherein said dispersion further comprises up to 0.5% of at least a stabilizer, and up to 2% of at least a polyol, percentage being expressed on a w/w basis relative to the total weight of the dispersion.

15. The core-shell microcapsule of claim 11, wherein step 2) is performed and the further $C_{1-4}$ compound is present in an amount of between about 5% and 100%, with the percentage being expressed on a w/w basis relative to the total weight of the oligomer composition.

16. The core-shell microcapsule of claim 1, wherein the oil phase includes a perfuming oil.

17. The core-shell microcapsule of claim 16, which are present in a perfuming composition that includes a perfumery base.

18. The core-shell microcapsule of claim 17, wherein the perfumery base is a perfume, a fabric care product, a body-care product, an air care product or a home care product.

19. The core-shell microcapsule of claim 1, which encapsulates an oil phase that includes a perfume oil and which is present in a perfume, a fabric care product, a body-care product, an air care product or a home care product.

* * * * *